US010338071B2

(12) United States Patent
Hahn et al.

(10) Patent No.: US 10,338,071 B2
(45) Date of Patent: Jul. 2, 2019

(54) COMPOSITIONS, METHODS AND MICROFLUIDICS DEVICE FOR TELOMERASE BASED IN VITRO DIAGNOSTIC ASSAYS FOR DETECTING CIRCULATING TUMOR CELLS (CTC)

(71) Applicant: The Trustees of the University of Pennsylvania, Philadelphia, PA (US)

(72) Inventors: Stephen M. Hahn, Glen Mills, PA (US); Jay F. Dorsey, Media, PA (US); Gary D. Kao, Wynnewood, PA (US); Emigdio Reyes, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 3 days.

(21) Appl. No.: 15/812,105

(22) Filed: Nov. 14, 2017

(65) Prior Publication Data

US 2018/0113130 A1 Apr. 26, 2018

Related U.S. Application Data

(62) Division of application No. 14/438,321, filed as application No. PCT/US2013/031698 on Mar. 14, 2013, now Pat. No. 9,846,157.

(Continued)

(51) Int. Cl.
*G01N 33/574* (2006.01)
*C12Q 1/6897* (2018.01)
(Continued)

(52) U.S. Cl.
CPC ...... *G01N 33/574* (2013.01); *B01L 3/502753* (2013.01); *C12Q 1/6897* (2013.01);
(Continued)

(58) Field of Classification Search
CPC ............ G01N 33/574; G01N 33/54366; B01L 3/502753; C12Q 1/6897; C12Q 1/68
(Continued)

(56) References Cited

U.S. PATENT DOCUMENTS

| 2002/0037280 A1 | 3/2002 | Lieber et al. |
| 2002/0102264 A1* | 8/2002 | Cheung .............. A61K 49/0004 424/155.1 |

(Continued)

FOREIGN PATENT DOCUMENTS

WO    WO-2000/46355 A2    8/2000

OTHER PUBLICATIONS

Bhang et al., Tumor-specific imaging through progression elevated gene-3 promoter-driven gene expression, Nature Medicine, vol. 17(1):123-129, Dec. 12, 2010.

(Continued)

*Primary Examiner* — Brian J. Sines
(74) *Attorney, Agent, or Firm* — Howson and Howson LLP; Cathy A. Kodroff

(57) ABSTRACT

A repeatable method for detecting circulating tumor cells in vitro is provided. The method involves combining a test sample from a patient suspected of having circulating tumor cells, and a non-lytic adenoviral system, and culture media for the cells. The adenoviral system utilizes (i) a first replication-defective adenoviral particle in which an expression cassette is packaged, said expression cassette comprising an adenoviral 5' and 3' ITRs and a tumor-specific promoter; and (ii) a coding sequence for a reporter protein which is expressed in the presence of circulating tumor cells, and an adenoviral 3' ITR. The test sample and the non-lytic adenoviral system are incubated for a sufficient time to permit expression of the reporter protein, and measuring reporter protein expression in the test samples, whereby (Continued)

presence of reporter expression indicates the presence of circulating tumor cells in the sample. Because the system is non-lytic, the testing can be repeated on the cells which remain viable in culture. Also provided is a method for enriching test samples having circulating tumor cells and a microfluidics device suitable for CTC-specification identification and enumeration.

43 Claims, 12 Drawing Sheets

Related U.S. Application Data

(60) Provisional application No. 61/718,993, filed on Oct. 26, 2012.

(51) Int. Cl.
  *C12Q 1/68* (2018.01)
  *G01N 33/543* (2006.01)
  *B01L 3/00* (2006.01)
  *G01N 30/52* (2006.01)

(52) U.S. Cl.
  CPC ........... *G01N 33/54366* (2013.01); *B01L 2200/0652* (2013.01); *B01L 2200/0668* (2013.01); *B01L 2300/0816* (2013.01); *B01L 2300/0864* (2013.01); *B01L 2400/0487* (2013.01); *B01L 2400/086* (2013.01); *G01N 2030/524* (2013.01)

(58) Field of Classification Search
  USPC ..... 422/502, 68.1; 436/43, 63, 64; 435/6.14, 435/6.11, 7.23
  See application file for complete search history.

(56) References Cited

U.S. PATENT DOCUMENTS

| | | |
|---|---|---|
| 2003/0054555 A1 | 3/2003 | Farmer et al. |
| 2003/0103963 A1* | 6/2003 | Cheung .............. A61K 49/0004 424/130.1 |
| 2006/0115623 A1 | 6/2006 | Aizenberg et al. |
| 2006/0160243 A1 | 7/2006 | Tang et al. |
| 2007/0026381 A1 | 2/2007 | Huang et al. |
| 2007/0026417 A1 | 2/2007 | Fuchs et al. |
| 2007/0135013 A1 | 6/2007 | Faris |
| 2007/0161051 A1 | 7/2007 | Tsinberg et al. |
| 2007/0172903 A1 | 7/2007 | Toner et al. |
| 2010/0310571 A1* | 12/2010 | Cheung .............. A61K 51/1078 424/141.1 |
| 2011/0284110 A1 | 11/2011 | Gagnon |
| 2012/0077246 A1 | 3/2012 | Hong et al. |
| 2013/0121895 A1 | 5/2013 | Tang et al. |
| 2013/0288273 A1* | 10/2013 | Takagi ................. G01N 33/574 435/7.23 |

OTHER PUBLICATIONS

Hearing et al., Identification of a Repeated Sequence Element Required for Efficient Encapsidation of the Adenovirus Type 5 Chromosome, Journal of Virology, vol. 61(8):2555-2558, Aug. 1, 1987.

Steinwaerder et al., DNA Replication of First-Generation Adenovirus Vectors in Tumor Cells, Human Gene Therapy, vol. 11:1933-1948, Sep. 1, 2000.

Steinwaerder et al., Tumor-specific gene expression in hepatic metastases by a replication-activated adenovirus vector, Nature Medicine, vol. 7(2):240-243, Feb. 1, 2001.

Alunni-Fabbroni et al., "Circulating tumour cells in clinical practice: Methods of detection and possible characterization", Methods, vol. 50(2010):289-297, Jan. 2010.

Bhang et al., "Tumor-Specific Imaging through Progression Elevated Gene-3 Promoter-Driven Gene Expression", Nat Med, vol. 17(1):123-129, Jan. 2011.

Su et al., "Targeting gene expression selectively in cancer cells by using the progression-elevated gene-3 promoter", PNAS, vol. 102(4):1059-1064, Jan. 2005.

Chen et al., "Nanoroughened Surfaces for Efficient Captre of Circulating Tumor Cells without Using Capture Antibodies", ACS Nano, vol. 7(1):566-575, Oct. 2012.

Thierry et al., "Herceptin functionalized microfluidic polydimethylsiloxane devices for the capture of human epidermal growth factor receptor 2 positive circulating breast cancer cells", Biomicrofluidics, vol. 4:032205-1-032205-10, Apr. 2010.

Wan et al., "Lab on a Chip: Electronic Supplementary Information, Capture, Isolation and Release of Cancer Cells with Aptamer-functionalized Glass bead Array", The Royal Society of Chemistry, Jan. 2012.

NIH Report, "Project Information 1R03CA165182-01 (Abstract)", Sep. 2012.

International Search Report and Written Opinion issued for International Patent Application No. PCT/US2013/031698, dated May 7, 2013.

\* cited by examiner

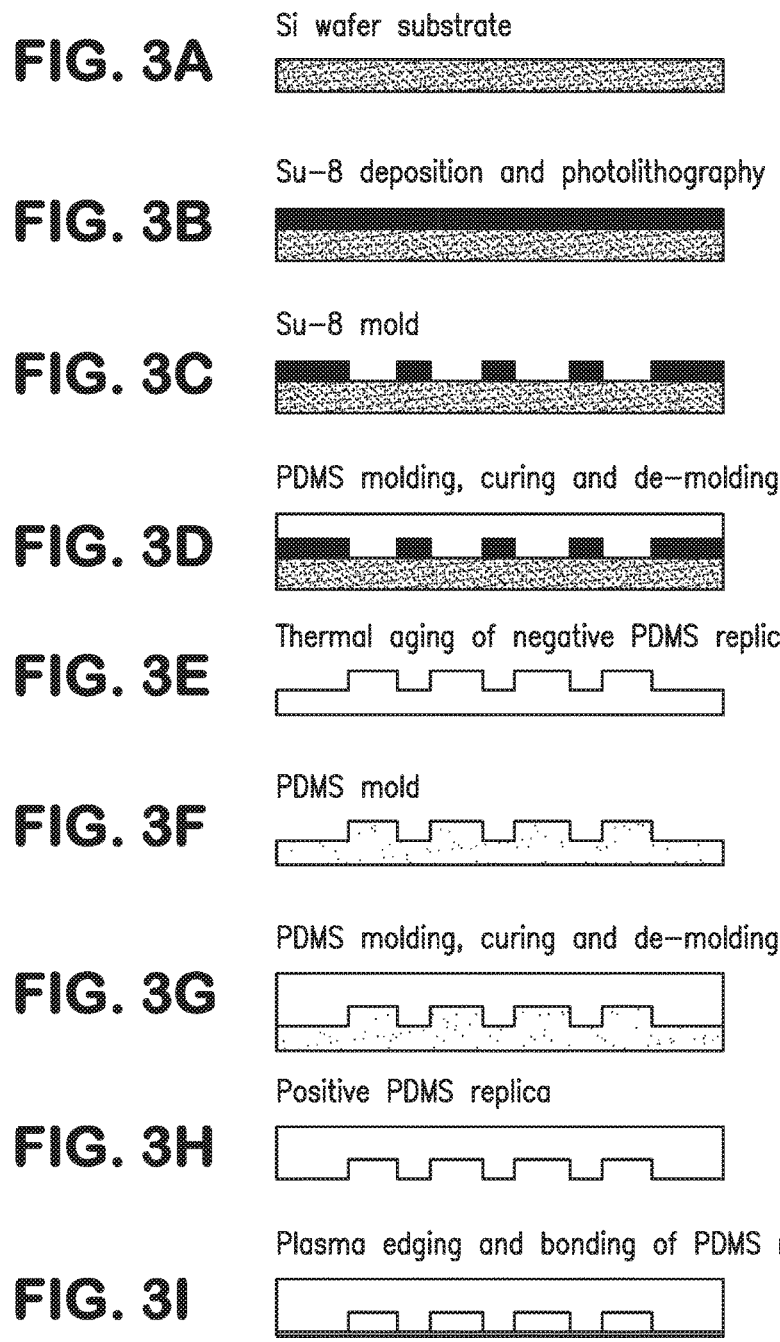

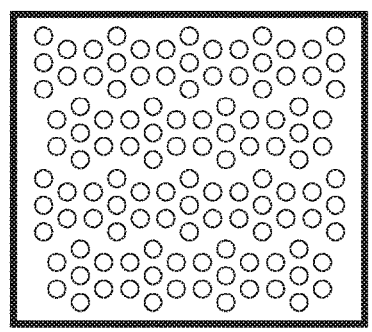
FIG. 5A
○  ⊥ 100 μm
FIG. 5B
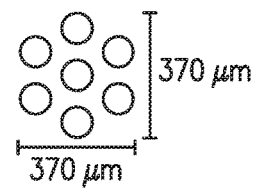
FIG. 5C
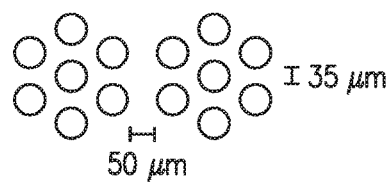
FIG. 5D

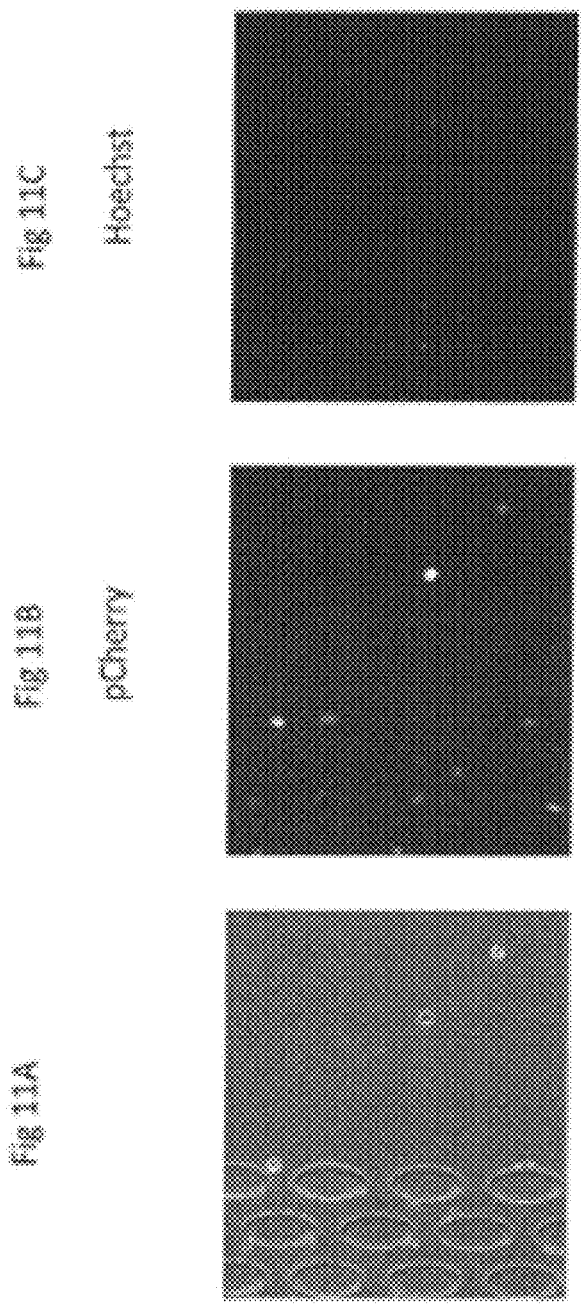

COMPOSITIONS, METHODS AND MICROFLUIDICS DEVICE FOR TELOMERASE BASED IN VITRO DIAGNOSTIC ASSAYS FOR DETECTING CIRCULATING TUMOR CELLS (CTC)

CROSS-REFERENCE TO RELATED APPLICATIONS

This application is a divisional of U.S. patent application Ser. No. 14/438,321, filed Apr. 24, 2015, which is a 371 of PCT/US13/31698, filed Mar. 14, 2013, now expired, which claims priority of U.S. provisional 61/718,993, filed Oct. 26, 2012, now expired. These applications are incorporated herein by reference in their entireties.

STATEMENT OF FEDERALLY SUPPORTED RESEARCH

This invention was made with government support under grant number R01CA145075 and K08 NS076548 awarded by the National Institutes of Health. The government has certain rights in the invention.

BACKGROUND OF THE INVENTION

From their formation and throughout their development, primary tumors shed cells that circulate through the bloodstream of cancer patients. These circulating tumor cells (CTCs) potentially hold important clinical information that can be used for detection, characterization, accurate treatment and monitoring of cancer. While the presence of CTCs in the blood has been documented for over 100 years and various methods have been described for their detection. [M. Alumni-Fabroni and M. Sandri, *Methods,* 50 (2010) 289-297], these traditional methods have low sensitivity. Consequently, much of the research of the past decades has been focused on the development of reliable methods for CTC enrichment and identification, mainly trying to overcome severe technical limitations.

In recent years, evidence supporting that the presence of CTCs in the blood can serve as a biomarker for potential disease and poor prognosis has continued to stimulate interest in the development of methodologies for detection and isolation of CTCs in blood samples from cancer patients. Another important attribute that has made the detection and isolation of CTCs attractive is the fact that despite of their heterogeneity, these cells may carry genetic information about the primary tumor that can be useful in guiding the treatment of a specific patient and providing an opportunity for individualize medicine. However, although many technologies have been recently developed recently for the detection and isolation of CTCs from peripheral blood samples of cancer patients, this task remains technically challenging.

This is mainly due to the fact that CTCs are rare and only occur at very low concentrations of one tumor cell per one billion blood cells. Typical methods for the identification and isolation of CTCs required extremely sensitive and specific analytical methods that generate very low yield and purity samples.

Circulating tumor cell (CTC) assays may powerfully improve the ability to monitor disease status, gauge prognosis, and guide treatment decisions for patients with cancer. However, CTC assays for many patients including those with brain tumors (such as Glioblastoma multiforme (GBM)) have not been possible due to the lack of surface expression of common biomarkers such as EpCAM to facilitate separation and subsequent detection. For other tumors such as non-small cell lung cancer (NSCLC), the ability to monitor treatment response may help reduce the lethality of lung cancer by overcoming limitations of imaging to monitor NSCLC disease state intra and post treatment, and avoid the need for a non-invasive means to assess NSCLC therapeutic effect and adjust the treatment plan accordingly.

The use of microfluidic devices for CTC detection and isolation has been described in the literature. In general, a microfluidic device handle relatively small cell numbers and sample volumes [e.g., from single cells to millions of cells, and from 10 to 200 microliters] making possible the detection and isolation of CTCs from a sample which may only contain few CTCs. Currently, some microfluidic systems have been described as useful for the detection of CTCs, including the CTC-Chip [S. Nagrath et al, "Isolating of rare circulating tumour cells in cancer patients by microchip technology", Nature, 450: 1235-1239 (20 Dec. 2007)], the herringbone-chip [S. L. Scott, et al, "Isolation of circulating tumor cells using a microvortex-generating herringbone chip, Proc Natl Acad Sci, vol. 107, no. 43, 18392-18397, e-pub Oct. 7, 2010, ahead of print Oct. 26, 2010] and the high-throughput microsampling unit (HTMSU) [A. Adams, et al, "Highly efficient circulating tumor cell isolation from whole blood and label-free enumeration using polymer-based microfluidics with an integrated conductivity sensor", J. Am. Chem. Soc., 2008 Jul. 9; 130(27): 8633-41]. However, these systems present major technical limitations including the inability to capture non-epithelial cells (e.g. cells which do not express epithelial cell adhesion molecule (EpCAM). Capture efficiency and purity also merit improvement (M. Alunni-Fabroni and M. T. Sandri, "Circulating tumor cells in clinical practice: Methods of detection and possible characterization" Methods, 2010 Jan. 29; 50(4): 289-297).

Thus, there is still a need for a microfluidic device capable of capturing both epithelial and non-epithelial CTCs with high efficiency that yields a CTCs sample with high purity for accurately characterizing the biology of CTCs and to develop CTC analysis methodologies that can help guide diagnosis and treatment in a clinical setting. In addition, methods for qualitatively and/or quantitatively assessing CTC of a variety of tumor origins are still needed.

SUMMARY OF THE INVENTION

The invention provides a repeatable method for detecting circulating tumor cells (CTC) in vitro. The method is repeatable because the cells are not lysed as part of the assay and thus can remain viable in culture to allow for secondary analysis.

In one aspect, the method involves combining a test sample from a patient suspected of having circulating tumor cells, a non-lytic adenoviral system, and culture media for the cells. The adenoviral system comprises: (i) a first replication-defective adenoviral particle having an adenoviral capsid in which an expression cassette is packaged, said expression cassette comprising an adenoviral 5' ITR, an tumor-specific promoter which is specifically activated in the presence of circulating tumor cells, and an adenoviral 3' ITR, wherein said adenoviral particle is rendered replication defective and non-lytic by a deletion in one or more adenoviral early genes; and (ii) a coding sequence for a reporter protein which is expressed in the presence of circulating tumor cells, and an adenoviral 3' ITR. Following this, the test sample and the non-lytic adenoviral system are incubated for a sufficient time to permit expression of the reporter protein. Additional culture media may be added or the culture media replenished. Reporter protein expression is measured in the test samples whereby presence of reporter expression indicates the presence of circulating tumor cells in the sample. In one example, the promoter is human telomerase reverse transcriptase (hTERT). One or more of these steps may be repeated, optionally using a second adenoviral system with a different reporter protein. The reporter protein may be under the control of the same or a different tumor specific promoter. Because the cells are not lysed in this assay, the first and/or any subsequent measurement may be performed after eighteen hours to ninety-six hours, or longer, after first combining the adenoviral system and the test sample.

In another embodiment, the invention provides a method for enriching a test sample from a patient suspected of having circulating tumor cells. The method involves obtaining a whole blood sample from a patient; combining the whole blood sample with neutral buffered saline in a tube having a gradient gel to separate out CTCs and white blood cells (WBCs) from red blood cells (RBCs), and a conical bottom; centrifuging the tube for about 10 minutes to about 60 minutes at about 500 relative centrifugal force (RCF) units to about 3000 RCF units; harvesting the CTC-enriched layer to obtain a CTC-enriched pellet suspension; incubating the pellet suspension in a water bath; and introducing cell culture media to allow pellet suspension in preparation for the adenoviral system.

In another aspect, the invention provides a product comprising an adenoviral vector system for use in a telomerase based assay for detecting circulating tumor cells in vitro. The adenoviral system is composed of, at a minimum, (a) a first replication-defective adenoviral particle having an adenoviral capsid in which an endonuclease expression cassette is packaged, said expression cassette comprising an adenoviral 5' ITR, an hTERT promoter sequence which is activated in the presence of circulating tumor cells, an endonuclease coding sequence under the direction of sequences which direct expression thereof, and an adenoviral 3' ITR, wherein said adenoviral particle is rendered replication defective by a deletion in one or more adenoviral early genes; and (b) a DNA molecule comprising an expression cassette for a reporter gene comprising a coding sequence for the reporter protein and sequences which direct expression thereof, said expression cassette flanked at its 5' and 3' ends by recognition sites for the endonuclease, and an adenoviral 3' ITR.

In one embodiment, the reporter expression cassette (b) is on a second replication-defective adenoviral particle. The endonuclease can be a recombinase. In one embodiment, the reporter gene is selected from the group consisting of a green fluorescent protein, enhanced green fluorescent protein, mCherry, red fluorescent protein, red fluorescent protein-turbo.

In still a further embodiment, the invention provides a microfluidic device for capturing circulating tumor cells (CTCs) from enriched samples. The devices is comprised of four capture channels containing different arrays of microcolumns of different geometrical shapes and chemically functionalized with a biotin-binding protein that mediates the capture of biotinylated-antibody coated CTCs. The capture channels are connected to an inlet and outlet reservoir through distribution channels that facilitate the transport of sample in and out of the capture channels. The arrangement of columns in this device is designed for maximal capture, with greatest efficiency and purity (specificity)

These and other aspects of the invention will be readily apparent from the following detailed description of the invention.

BRIEF DESCRIPTION OF THE DRAWINGS

FIG. 3A-FIG. 3I provide a schematic illustration of the double casting prototyping by thermal aging of PDMS process utilized for the fabrication of the PDMS cast used to make the microfluidic device described herein. The process is stated with a silica (Si) wafer substrate (FIG. 3A). FIG. 3B illustrates Su-8 [a negative, epoxy-type photoresist based on EPON SU-8 epoxy resin developed by and patent by IBM (U.S. Pat. No. 4,882,245—1989)] deposition and photolithography on the Si wafer substrate.

FIG. 3C illustrates the Su-8 mold. FIG. 3D illustrates the use of the Su-8 mold for PDMS molding, curing and de-molding. FIG. 3E illustrates the thermal aging of the negative PDMS replica of the Su-8 mold. FIG. 3F illustrates the resulting thermally aged PDMS replica which serves as a mold to case a second PDMS replica with positive orientation (FIG. 3H). FIG. 3I illustrates the plasma edging and bonding of the positive PDMS cast or replica of FIG. 3H to a glass slide.

FIG. 4A provides a top view of the reservoir and distribution channel system. FIG. 4B provides a top view of the capture channels contained within the microfluidic device. FIG. 4C provides a cross-sectional view of a capture channel of the device.

FIGS. 5A-5D provide enlarged views of the cylindrical microcolumns in one of the channels of the device of FIG. 2. FIG. 5A illustrates the shape and pattern of the cylindrical microcolumns. FIG. 5B is a further enlarged view of FIG. 5A and illustrates the size of one of the cylindrical shapes. FIG. 5C is an alternative further enlarged view of FIG. 5A and illustrates a hexagonal-shaped unit of the cylindrical microcolumns. FIG. 5D is also an alternative further enlarged view of FIG. 5A and illustrates the separation between the hexagonal units.

FIG. 6A illustrates the shape and pattern of the elliptical microcolumns. FIG. 6B is a further enlarged view of a single elliptical depression. FIG. 6C is an alternate further enlarged view of FIG. 6A and illustrates the separation between elliptical microcolumns from neighboring columns within a row and between rows.

FIG. 7A illustrates the shape and pattern of the triangles and chevron-like microcolumn. FIG. 7B is a further enlarged view of FIG. 7A showing the size and shape of a triangle. FIG. 7C is a further enlarged view of FIG. 7A showing the size and shape of a chevron. FIG. 7D is a further enlarged view of FIG. 7A illustrating a triangle and chevron pattern, including orientation.

FIG. 8A the triangle and chevron pattern, which are in the opposite orientation to that of FIGS. 7A-D. FIG. 8B is a further enlarged view of FIG. 8A showing the size between the two triangle-chevron units and the space between the rows. FIG. 8B is a further enlarged view of FIG. 7A showing the size and shape of the chevron. FIG. 8C is a further enlarged view of FIG. 8A illustrating the total size of a two triangle-chevron unit, including the distance between the two triangle, and between the triangles and the chevron.

FIGS. 11A-11C are gray scale images in bright field (FIG. 11A) and fluorescence red (FIG. 11B) and blue (FIG. 11C) optic channels of cells captured at the surface of elliptical microcolumns in one of the capture channels. FIG. 11A is a grayscale version of the bright field image which illustrates that the captured cells are attached to different surfaces in the capture channel including the walls of the microcolumns and the floor of the channel. FIG. 11B shows in grayscale that the immobilized cells are positive for pCherry as shown in the fluorescence image taken with the red optics channel suggesting that they were captured via biotin-NeutrAvidin chemistry. In addition, fluorescence image taken with blue optics channel (FIG. 11C) confirms most of the captured cells are pCherry positive since all fluorescent points in this image dots to the fluorescent dots found in the red optics channel image, thus suggesting high purity (in terms of infected cells only, not Jurkats) of the captured cells.

DETAILED DESCRIPTION OF THE INVENTION

Figure 1:
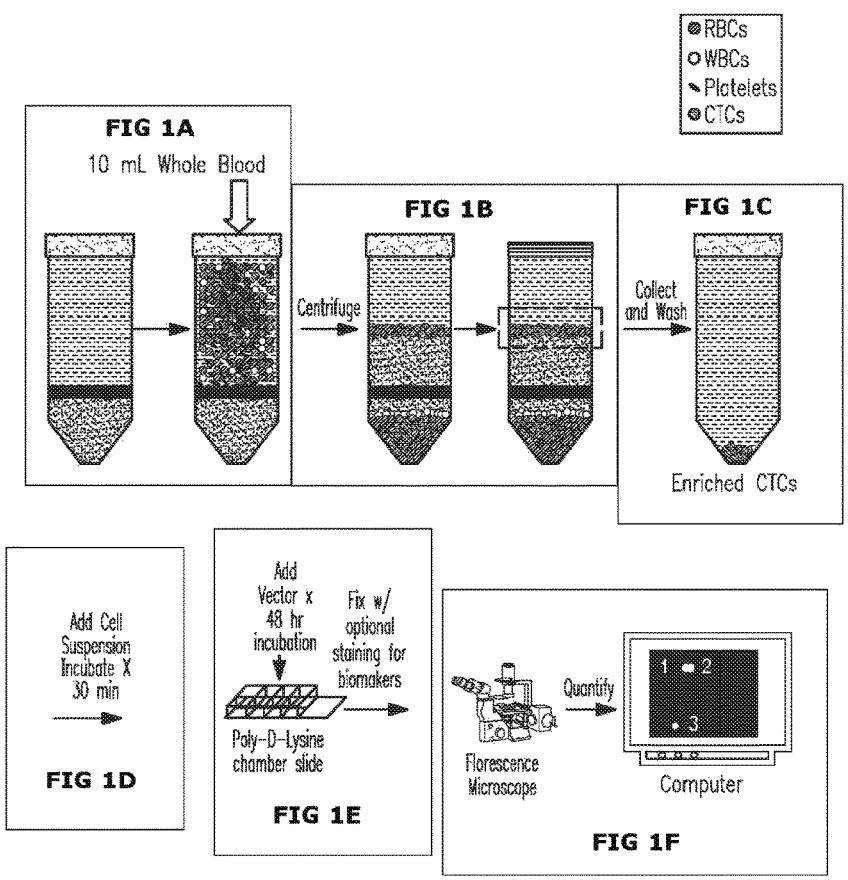
FIG. 1A-FIG. 1F illustrates a CTC analysis performed according to the invention. This illustrates the CTC-enrichment method (steps A to C) which include collection of whole blood (A), centrifuging in a tube with a gradient gel which separates CTC and white blood cells from red blood cells (B), collection of the CTC-enriched layer and washing (C). Steps (D)-(F) illustrate the CTC detection method of the invention, including suspending the CTC test sample in media and incubating prior to placing in the test vessel (D), adding the adenoviral vector system and incubating (E), detecting fluorescence (F) and optionally quantifying using a computer.

The present invention provides a method for detecting circulating tumor cells (CTCs) in vitro in a non-lytic system. Because the system is non-lytic it offers additional flexibility in terms of timing of when the detection step may be performed and also offers additional opportunity to verify and quantify CTCs, because the assay may be repeated on the same test sample because the cells of the test sample can be maintained in culture. The system utilizes a non-lytic adenoviral vector system. Further, the invention provides a method for treating a sample in order to enrich CTC and increase sensitivity and accuracy of measurement. The enriched sample may thereafter be assessed using conventional microscopy techniques. Alternatively, CTCs from the enriched sample may be assessed and enumerated using a microfluidics device of the invention.

In one embodiment, the method for detecting CTC involves combining a test sample from a patient suspected of having circulating tumor cells, a non-lytic adenoviral system, and culture media for the cells. Suitably, the adenoviral system is composed of a replication-defective adenoviral particle having an adenoviral capsid in which an expression cassette is packaged. The adenoviral vector contains an adenoviral 5' ITR, a tumor-specific promoter which is specifically activated in the presence of circulating tumor cells, and an adenoviral 3' ITR. The adenoviral particle is rendered replication defective and non-lytic, e.g., by a deletion in one or more adenoviral early genes. The adenoviral vector system further comprises a coding sequence for a reporter protein which is specifically expressed in the presence of circulating tumor cells, and an adenoviral 3' ITR. The test sample and the non-lytic adenoviral system are incubated for a sufficient time to permit expression of the reporter protein, during which time the cells are maintained by replenishment or addition of fresh media. Following incubation, reporter protein expression is measured in the test samples. Since expression of the reporter gene is under the specific control of a tumor associated promoter or a telomerase promoter, reporter gene expression indicates tumor cells in the sample. These steps may optionally be repeated.

Non-lytic Adenoviral Vector Systems:

The method of the invention utilizes an adenoviral vector system in which the adenoviral vector is rendered replication-defective in a manner which prevents its ability to lyse the target cells while still permitting efficient infection thereof. Several variants of the adenoviral vector system are provided by the present invention. In one embodiment, the assay utilizes a single adenoviral vector. However, even in embodiments which utilize two or more, i.e., multiple, replication-defective adenoviral vectors, each of the adenoviral vectors is permits the cells to be infected and the assay to proceed to CTC detection without cell lysis.

The adenoviral vector system utilizes one or more adenoviral particle, which particle has an adenoviral capsid into which is packaged selected adenoviral nucleic acid sequences which have had the regions responsible for replication function ablated, either by deletion of adenoviral coding regions, or by insertion and disruption of the coding regions. In one embodiment, the adenoviral particles are rendered replication-defective by deletions in one, or preferably both, the E1a and/or E1b genes. Alternatively, the adenoviruses are rendered replication-defective by another means, optionally while retaining the E1a gene or E1b gene (e.g., an insertion which disrupts expression of the E1a and/or E1b gene product). Similarly, in some embodiments, reduction of an immune response to the vector may be accomplished by deletions in the E2b and/or DNA polymerase genes. The adenoviral vectors can also contain other mutations to the adenoviral genome, e.g., temperature-sensitive mutations or deletions in other genes.

The adenoviral vector systems are designed so that a reporter is expressed in the presence of circulating tumor cells, but not in the absence of such CTCs. In order to accomplish this, the adenoviral vector system is designed so that the reporter is expressed under the control of a promoter which is specifically activated in the present of circulating tumor cells. In one embodiment, the promoter is a telomerase-associated promoter, such as human telomerase reverse transcriptase (hTERT) [Lim, K. W., et al, Coexistence of two distinct G-quadruplex conformations in the hTERT promoter, J. Am. Chem. Soc. 132 (35), 12331-12342 (2010); U.S. Pat. No. 6,610,839], a human telomerase RNA (hTR), a hTERC promoter [Glasspool, R M, et al, "The hTERT and hTERC Telomerase Gene Promoters Are Activated by the Second Exon of the Adenoviral Protein, E1A, Identifying the Transcriptional Corepressor CtBP as a Potential Repressor of Both Genes", Neoplasia. 2005 June; 7(6): 614-622], and a progression elevated gene promoter (PEG-Prom) [See, e.g., US2004/0203066A1, for the sequences of the rat PEG-Prom promoter; Su Z Z, et al, Proc Natl Acad Sci USA. 2005 Jan. 25; 102(4):1059-64. Epub 2005 Jan. 12. "Targeting gene expression selectively in cancer cells by using the progression-elevated gene-3 promoter"]. For convenience in this specification, reference will be made to a telomerase-specific promoter. However, it will be understood that tumor specific promoters may also be utilized in the constructs and methods described herein.

Suitably, this promoter is operably linked to the sequence encoding a reporter protein. In one embodiment, the reporter protein is a fluorescent protein. A variety of fluorescent proteins have been described in the literature. These proteins and their coding sequences are available from a variety of sources including commercial sources such as, e.g., BioVision, EMD Millipore, Invitrogen, amongst other sources. Suitable proteins include, green fluorescent protein, enhanced green fluorescent protein, mCherry, red fluorescent protein, and red fluorescent protein-turbo, amongst others. However, other suitable proteins may be selected.

| Fluorescent Proteins and Properties Thereof | | | | | | |
|---|---|---|---|---|---|---|
| Protein (Acronym) | Excitation Maximum (nm) | Emission Maximum (nm) | Molar Extinction Coefficient | Quantum Yield | in vivo Structure | Relative Brightness (% of EGFP) |
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| Emerald | 487 | 509 | 57,500 | 0.68 | Monomer* | 116 |
| Superfolder GFP | 485 | 510 | 83,300 | 0.65 | Monomer* | 160 |
| Azami Green | 492 | 505 | 55,000 | 0.74 | Monomer | 121 |
| mWasabi | 493 | 509 | 70,000 | 0.80 | Monomer | 167 |
| TagGFP | 482 | 505 | 58,200 | 0.59 | Monomer* | 110 |
| TurboGFP | 482 | 502 | 70,000 | 0.53 | Dimer | 102 |
| AcGFP | 480 | 505 | 50,000 | 0.55 | Monomer* | 82 |
| ZsGreen | 493 | 505 | 43,000 | 0.91 | Tetramer | 117 |
| T-Sapphire | 399 | 511 | 44,000 | 0.60 | Monomer* | 79 |
| Blue Fluorescent Proteins | | | | | | |
| EBFP | 383 | 445 | 29,000 | 0.31 | Monomer* | 27 |
| EBFP2 | 383 | 448 | 32,000 | 0.56 | Monomer* | 53 |
| Azurite | 384 | 450 | 26,200 | 0.55 | Monomer* | 43 |
| mTagBFP | 399 | 456 | 52,000 | 0.63 | Monomer | 98 |
| Cyan Fluorescent Proteins | | | | | | |
| ECFP | 439 | 476 | 32,500 | 0.40 | Monomer* | 39 |
| mECFP | 433 | 475 | 32,500 | 0.40 | Monomer | 39 |
| Cerulean | 433 | 475 | 43,000 | 0.62 | Monomer* | 79 |
| mTurquoise | 434 | 474 | 30,000 | 0.84 | Monomer* | 75 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| TagCFP | 458 | 480 | 37,000 | 0.57 | Monomer | 63 |
| mTFP1 (Teal) | 462 | 492 | 64,000 | 0.85 | Monomer | 162 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| TagYFP | 508 | 524 | 64,000 | 0.60 | Monomer | 118 |
| PhiYFP | 525 | 537 | 124,000 | 0.39 | Monomer* | 144 |
| ZsYellow1 | 529 | 539 | 20,200 | 0.42 | Tetramer | 25 |
| mBanana | 540 | 553 | 6,000 | 0.7 | Monomer | 13 |

-continued

Fluorescent Proteins and Properties Thereof

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| Orange Fluorescent Proteins | | | | | | |
| Kusabira Orange | 548 | 559 | 51,600 | 0.60 | Monomer | 92 |
| Kusabira Orange2 | 551 | 565 | 63,800 | 0.62 | Monomer | 118 |
| mOrange | 548 | 562 | 71,000 | 0.69 | Monomer | 146 |
| mOrange2 | 549 | 565 | 58,000 | 0.60 | Monomer | 104 |
| dTomato | 554 | 581 | 69,000 | 0.69 | Dimer | 142 |
| dTomato-Tandem | 554 | 581 | 138,000 | 0.69 | Monomer | 283 |
| TagRFP | 555 | 584 | 100,000 | 0.48 | Monomer | 142 |
| TagRFP-T | 555 | 584 | 81,000 | 0.41 | Monomer | 99 |
| DsRed | 558 | 583 | 75,000 | 0.79 | Tetramer | 176 |
| DsRed2 | 563 | 582 | 43,800 | 0.55 | Tetramer | 72 |
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| Red Fluorescent Proteins | | | | | | |
| mRuby | 558 | 605 | 112,000 | 0.35 | Monomer | 117 |
| mApple | 568 | 592 | 75,000 | 0.49 | Monomer | 109 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| dKeima-Tandem | 440 | 620 | 28,800 | 0.24 | Monomer | 21 |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |

*Weak Dimer

Where the assay is performed multiple times with different reporter genes, or where a multi-adenoviral system is utilized which also utilizes two or more different reporter genes, it is desirable that the proteins used are readily distinguishable from one another. For example, one may select a green fluorescent protein and a red fluorescent protein; or a green fluorescent protein and a yellow fluorescent protein, or a tangerine fluorescent protein and a yellow fluorescence protein. Still other suitable combinations may be selected.

In yet another embodiment, the vector system expresses a fusion protein which comprises a protein, polypeptide or peptide fused in frame to a fluorescent protein or a fragment thereof which functions (fluoresces) in the cell fused. In one embodiment, the fusion partner for the fluorescent protein or functional fragment thereof is an epithelial cell adhesion molecule such as EpCAM, or a functional fragment thereof. Such fusion proteins may be constructed using techniques such as described in C. Y. Wang, et al, 2004 November; 20(6): 765-768; K. Slanchev et al, PLoS Genet 2009.

The vector system provides a sequence encoding a reporter which is expressed directly or indirectly under the control of a telomerase-specific promoter. The expression cassette with the reporter coding sequence also may contain other regulatory control sequences necessary for expression of the reporter protein, including, e.g., an enhancer, a polyA, amongst other elements.

The reporter sequence may be located in the site of one of the deleted adenovirus early genes, e.g., E1a, E1b, E2a, E3, or E4a. Optionally, an adenovirus may contain two more reporter gene expression cassettes located either in tandem or in different adenovirus early gene sites (e.g., both in the E1 region and in E3) of a single adenovirus vector.

In another embodiment, a single adenovirus contains two different expression cassettes located in different early gene sites. In this embodiment, a first expression cassette contains the inducing or regulating agent under the control of a telomerase specific promoter and a second expression cassette contains a reporter gene under the control of an inducible or regulatable system. In this embodiment, the expression cassette with the inducing agent to be located in the site of the adenovirus E1 deletion and the expression cassette with the fluoroprotein coding sequence to be in the site of the adenovirus E3 deletion. However, other arrangements in the adenovirus may be engineered by one of skill in the art utilizing known genetic engineering and recombinant techniques. In one embodiment, a single adenovirus system with the dual cassette system can provide self-amplifying effects. The principle of this vector system is that when Telomerase activity is present in a transduced cell (such as a CTC), the promoter (e.g., hTERT) is activated and drives expression of the nuclease. The nuclease then causes inversion of a previously inverted fluorescent protein cassette (flanked by the two nuclease recognition sites), inducing expression of the Fluor-Protein. The inversion of the Fluor-Protein cassette then allows expression of the Fluor-Protein and consequently the targeted CTC fluoresces and is detectable.

In one embodiment, the fluoro-protein cassette is under the control of a constitutive promoter which drives its expression. In one embodiment, the promoter is a strong constitutive promoter, e.g., the CAGS promoter, which composed of the chicken β-actin promoter with human cytomegalovirus immediate early (CMVIE) enhancer.

In still another embodiment, this two expression cassette system may be carried by two different adenoviruses, one which carries the expression cassette with the reporter gene in an inducible or regulatable system and a second adenovirus which carries the inducing or regulating agent which is expressed by a telomerase specific promoter in the presence of tumor cells. Optionally, each of the adenoviruses contains two or more copies of the reporter gene or the inducing/regulating agent, respectively. When utilizing a multiple vector system, the two expression cassettes may each be located within the E1 region of their respective adenoviruses. Alternatively, the site of the E3 deletion may be selected for insertion of the expression cassette in one or more than one of the adenoviruses.

As described herein, the reporter protein may be controlled by an expression control system. In one embodiment, the expression cassette for the marker gene contains an endonuclease recognition site located both 5' and 3' to the coding sequence for the reporter protein and its upstream expression control sequences (e.g., promoter, any enhancer, intron) and the other expression cassette in the system contains an endonuclease coding sequence under the control of the telomerase specific promoter. The regulatable system can be selected from a tet-on/off system, a tetR-KRAB system, a mifepristone (RU486) regulatable system, a tamoxifen-dependent regulatable system, a rapamycin-regulatable system, or an ecdysone-based regulatable system. In one embodiment, the system utilizes an endonuclease, a recombinase, a meganuclease, or a zinc finger endonuclease that binds to the ablation recognition site in the first transcription unit and excises or ablates DNA and an interfering RNA, a ribozyme, or an antisense that ablates the RNA transcript of the reporter expression cassette. In one embodiment, the endonuclease is a Cre recombinase and the recognition sites flanking the reporter transgene are loxP sites. In another embodiment, endonuclease is FLP and the recognition site is FRT. In another embodiment, the endonuclease is a chimeric endonuclease such as that described in WO 2011/126808 A2. Another suitable endonuclease may be selected from among intron endonucleases, such as, e.g., I-TevI. Still other suitable nucleases include, e.g., integrases (catalyze integration), serine recombinases (catalyze recombination), tyrosine recombinases, invertases (e.g. Gin) (catalyze inversion), resolvases, (e.g., Tn3), and nucleases that catalyze translocation, resolution, insertion, deletion, degradation or exchange. Such nucleases have been described in the literature and are available from a variety of commercial sources.

In another embodiment, the reporter protein is expressed under the control of a constitutive promoter, e.g., when a dual or multi-vector system is utilized. Examples of constitutive promoters include, without limitation, the TBG promoter, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen]. A number of other expression control sequences, including promoters which are native and/or tissue-specific, are known in the art and may be utilized.

Expression control sequences include appropriate transcription initiation, termination, promoter and enhancer sequences; efficient RNA processing signals such as splicing and polyadenylation (polyA) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. One can enhance expression of desired proteins by known means to enhance the effectiveness of this system. For example, using the Woodchuck Hepatitis Virus Posttranscriptional Regulatory Element (WPRE). In a further embodiment, other expression control elements, such as enhancer elements, polyadenylation sites or Kozak consensus sequences may also be used to mimic the native expression.

In a vector system of the invention which utilizes two or more non-lytic adenoviruses, the vector elements of the two adenoviruses may be independently selected. The use of two different reporter genes has also been described for use in sequential assay steps. These two different reporter genes may be under the control of the same or different tumor specific promoters and/or the same or different nucleases. This may also be true of a single adenoviral vector containing two different reporter genes within a single adenoviral particle. In such an instance, the reporter genes are distinguishable from one another. Further, the invention contemplates the use of two or more non-lytic adenoviruses, whether used sequentially or simultaneously, in which two different reporter genes are under control of two different promoters. For example, a first reporter gene may be expressed in the presence of a telomerase-specific promoter and a second reporter gene may be selected which is expressed only in the presence of a specific type of tumor. Still other variations will be apparent to one of skill in the art in view of the information provided herein.

III. Production of Replication-Defective Adenoviruses

Replication-defective adenoviral vectors may be produced using methods which are known in the art, e.g., through use of adenoviral plasmids. In one embodiment, the adenoviral vectors are adenoviral particles which are rendered replication-defective by deletions in the E1a and/or E1b genes. The particle is composed of an adenoviral capsid which directs targeting of the adenoviral vector. Because this assay is performed in vitro, limitations on in vivo use of adenoviruses based on pre-existing immunity in the patient population to the adenovirus capsid (and particularly the capsid) are not a factor in the selection of the adenovirus source for the non-lytic vectors described herein. Rather, adenoviruses are selected taking into consideration such factors as ease of production and ability to target and infect cells efficiently. In the examples described herein, is adenovirus is human adenovirus 5 [VR-5, American Type Culture Collection]. However, an adenovirus from another source, particularly those naturally or modified to have particular affinity for circulating tumor cells in mammals, including humans, may be readily selected. Such an adenovirus may be of human origin, including, without limitation, Ad2, Ad31, Ad36 and Ad37. In other embodiments, the adenovirus may be of simian or another animal origin. Examples of suitable simian adenoviruses include those described in, e.g., U.S. Pat. No. 8,105,574 (Pan5, Pan6, Pan7, SV1, SV25, SV39), WO 2012/071318 (A1321, A1325, A1295, A1316, A1322), WO 2009/073104; WO 2009/105084; and WO 2009/073102. Still other adenoviruses are known and may be obtained from a variety of sources including the ATCC, commercial and academic sources, or the sequences of the Ad may be obtained from GenBank or other suitable sources. The adenoviral vectors can also contain other mutations to the adenoviral genome, e.g., temperature-sensitive mutations or deletions in other genes. In other embodiments, it is desirable to retain an intact E1a and/or E1b region in the adenoviral vectors. Such an intact E1 region may be located in its native location in the adenoviral genome or placed in the site of a deletion in the native adenoviral genome (e.g., in the E3 region).

Thus, one embodiment, the system incorporates a vector in which the viral sequences contain mutation that renders it temperature sensitive. At the lower "permissive" temperature of 32° Celsius, the virus is able to replicate within transduced cells and thus amplify the fluorescent signal. However, before the replication process can proceed to cell lysis (and thus death of the transduced CTC), the cells are shifted to the higher "non-permissive" temperature of 37° C. At that higher temperature, all replication ceases and the CTCs should stay intact. This system has the potential weakness however of "leakiness", in which a degree of viral replication may still occur at the higher temperature, resulting in CTC lysis. There is also the technical difficulty that the image acquisition and analysis and subsequent processing of CTCs may unavoidably involve conditions that make maintaining the higher non-permissive temperature not possible.

A range of adenovirus nucleic acid sequences can be employed in the vectors. For example, all or a portion of the adenovirus delayed early gene E3 may be eliminated from the adenovirus sequence which forms a part of the recombinant virus. The function of an E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the adenovirus genome. Similarly, deletions in the intermediate genes IX and IVa$_2$ may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the adenovirus gene content of the viral vectors employed to carry the expression cassette, a helper adenovirus or non-replicating virus fragment may be necessary to provide sufficient adenovirus gene sequences necessary to produce an infective recombinant viral particle containing the expression cassette. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 374: 16985-16987 (1989); K. J. Fisher and J. M. Wilson, *Biochem. J.*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the Ad vector. This is particularly advantageous because, due to the diversity between the Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products that can be utilized for production of an E1-deleted adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from the same adenovirus as supplies the adenoviral vector capsid or a transcomplementary adenovirus under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired adenoviral gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), *Hum Gene Ther*, 9:1909-1917], Saos, C2Cl2, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering a vector for production of the adenoviral particle, the adenoviral vector is delivered in an amount from about 5 μg to about 100 μg DNA, and preferably about 10 to about 50 μg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

The packaging or production vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired expression cassette-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. However, the invention is not limited to the method for production of the adenoviral vectors.

The resulting replication-defective adenoviruses are useful in the methods of the system and assay of invention.

Circulating Tumor Cell (CTC) Test Sample Preparation and CTC Detection Assay:

The invention utilizes one or more adenoviruses which have been rendered non-lytic and which specifically express a fluorescent protein in the presence of circulating tumor cells to qualitatively and quantitatively detect the presence of CTCs. As described above, the method for detecting circulating tumor cells in vitro involves combining a test sample from a patient suspected of having circulating tumor cells and a non-lytic adenoviral system in a well, tube or another vessel containing media sufficient to permit infection of the cells and sustain the cells throughout the assay period. The test sample and the non-lytic adenoviral system are incubated under conditions which permit cell infection and which permit expression of the reporter protein. The cell media may be replaced or replenished as needed throughout this process. After the desired incubation period, reporter protein expression is measured in the test samples. As described herein, because the system is non-lytic, the steps described herein, including infection, incubation and/or measurement steps may be optionally repeated, either with the same or a different non-lytic reporter adenovirus system.

CTC Enrichment

In one embodiment, a whole blood sample is taken from a subject and enriched prior to being used as a test sample in the method described herein. This is done because of the relatively low number of circulating tumor cells in the bloodstream and to improve the accuracy of results. Various techniques and apparatus for enriching samples with circulating tumor cells have been described in the literature, including specially engineered parlene membrane microfilters [Lin L K, et al, Clin Cancer Res, 2010, 16(20):5011-5018], a density gradient separation method which is commercially available as OncoQuick® tubes [Greiner Bio-One, Frickenhausen, Germany], a CellSearch system (Vendex LLC), which relies on ferrofluid particles coated with epithelial cell adhesion molecule (EpCAM) antibodies to magnetically extract CTCs [Allard W J, et al, Clin Cancer Res, 2004 Oct. 15; 10(20): 6897-6904], a circulating tumor cell microchip, which utilizes anti-EpCAM antibodies bound to a silicon-based microchip over which blood samples are passed [Nagrath L V et al, Nature 2007; 450 (7173): 1235-1239]. Still other cell enrichment and extraction methods are described by Mikolajczyk et al [Mikolajczyk D S, et al, J Oncol 2011; 2011: 252361]. However, while these methods can be used in conjunction with the CTC detection assay of the method, none of these methods are as optimal of the CTC enrichment method described in the present application.

For the CTC enrichment of the present invention, a whole blood sample is obtained from a patient. Typically, between about 1 mL to about 15 mL, or about 5 mL to 12 mL, or about 10 mL is drawn. The blood sample this combined with a neutral buffered saline. For example, phosphate buffered saline may be selected. Alternatively, another buffered saline may be used. In one embodiment, approximately equivalent amounts of the blood and buffered saline are combined. However, variations on this combination may be selected, e.g., where more blood or more buffered saline are used. The blood-saline mixture are optionally typically chilled to about 0° C. to about 4° C. prior to centrifuging. The blood-saline mixture is placed in a test tube with a conically shaped bottom, which tube contains a density gradient separation fluid and a rigid but porous disk that minimizes mixing of blood with the gradient separation medium while the blood mixture is being added to the tube. A suitable system is commercially available from OncoQuick®. However, other separation systems could be substituted therefor. The tube is then centrifuged to separate the CTC from peripheral blood cells without lysing the cells, including, e.g., hematopoietic cells, erythrocytes, and granulocytes. In one embodiment, the tube is centrifuged for about 10 minutes to about 60 minutes at about 500 relative centrifugal force (RCF) units to about 3000 RCF units. In one embodiment, centrifuging is performed for about 20 minutes at about 1500 RCF units. However, the times and RCF units described herein can be varied to achieve cell separation while avoiding cell lysis or disruption. The enriched CTCs layer is harvested, typically in the form of a CTC-enriched pellet suspension. The CTC-enriched pellet is resuspended, and may be incubated in a water bath into which cell culture media is introduced to allow pellet suspension in preparation for the adenoviral system. Such a water bath is typically at about body temperature (e.g., about 35° C. to about 40° C., more preferably about 37° C.), although variations are permitted. In certain embodiments, following collection of the first CTC-enriched pellet suspension, the remaining solution is extracted and placed in a separate vessel, and the original vessel is washed in order to recapture any residual CTCs which are subsequently processed as described for the other CTCs and combined with the first CTC-enriched pellet suspension for inclusion in the test sample.

The enriched CTC test sample and culture media are aliquotted into chamber wells, a petri dish, tube, or another suitable vessel for conducting the CTC detection assay of the present invention. Whether using a single non-lytic adenovirus system or a multiple non-lytic adenovirus system as used herein, the total of adenoviruses combined with the test sample is about $10^5$ to about $10^{14}$ adenoviral genomes (GC) or viral particles (VP), about $10^7$ to about $10^{12}$ GC or VP, or about $10^8$ to about $10^{10}$ GC or VP, per 50 μL. Each well may have about 1000 to about 1,000,000 (total) cells; this typically includes both white blood cells and CTCs. In one embodiment, adenovirus vectors are introduced at a concentration of $2\times10^8$ viral particles/50 μL. The adenoviral vectors may be combined together and added simultaneously to the cells, or combined separately into the cells, such that the combined amount of adenoviruses added to the cells is within ranges set forth above. The ratio of two different adenoviral vectors may be about 2:about 1 to about 1:about 2 VP, or this ratio may be varied. For example, in one embodiment, two different adenoviral vectors are added in a ratio of about 1 to about 1. In another embodiment, e.g., where the system is self-amplifying, it may be desirable to have a ratio of about 2:about 1, wherein the amount of vector containing the nuclease is present in an amount of about 2 times the amount of the adenovirus with the marker gene.

The test sample is then incubated under conditions suitable to permit continued cell viability. In one embodiment, the cells are incubated for about eighteen hours to ninety-six hours, or about twenty-four hours to thirty-six hours, before measuring reporter expression levels. However, shorter or longer incubation times may be selected. For example, when using a single adenoviral vector system which does not self-amplify, it may be desirable to use longer incubation times and to select proteins which have high signal to noise ratios (e.g., bright fluorescence against low background autofluorescence).

Optionally, incubation is at about 37° C. in a humidified chamber under 5% $CO_2$, but other suitable conditions may be selected after first combining the adenoviral system and the test sample. Following incubation, expression of the report may be performed using methods such as are known in the art including, e.g., a fluorescent microscopy imaging. The assay may be repeated a second time, or more, using the same, or a different non-lytic adenoviral system of the invention, optionally with a different fluorescent protein than in the first non-lytic adenoviral system. Following imaging, the reaction vessel (e.g., chamber wells) can be fixed and counterstained to qualitatively assess isolated circulating tumor cells. The shape, size, and appearance of each fluorescent object helps confirm that individual CTCs are detected, and so that debris, parts of cells, or clumps of cells can be excluded from the analysis. A number of computer programs and algorithms are available which assist in enumeration by established parameters including fluorescent intensity, cell area, and cell diameter, such as IP Lab (Scanalytics (Spectra Services)).

The imaging described above can show both white blood cells (WBCs) and CTCs, e.g. on light (phase) microscopy, or under fluorescent microscopy if the nuclei of both WBCs and CTCs are stained with a nuclear marker such as Hoechst or DAPI dye. However, only the CTCs will show fluorescence, such as GFP, due to the telomerase activity driving the vector system. In contrast, the WBC will not be fluorescent or show only background fluorescence. The number of cells that express GFP under these conditions can then be counted and calculated as the number of CTCs per ml of original blood from the patient at the beginning of the assay. Secondary staining may also be performed, to further confirm the nature of the CTCs. For example, the purified cells can be stained for EpCAM (e.g. for lung cancer) or Nestin (for Glioblastoma Multiforme (GBM)). WBCs would not stain for EpCAM and Nestin, while CTCs would show both GFP and the stain for the secondary marker (which in turn is detected with secondary antibodies conjugated to a different fluorochrome, such as RFP). Alternatively, the WBCs can be stained for a WBC marker such as CD45, which would not be expressed by the CTC. Consequently, a typical result could consist of GFP-expressing CTCs do not show CD45, in the midst of many CD45-expressing WBCs that do not show GFP.

In a further embodiment, the invention provides a product comprising a novel vector system for use in a telomerase based assay for detecting circulating tumor cells in vitro. The product may contain one or more non-lytic adenoviral particles, optionally in freeze-dried state; a suspending agent; tubes, pouches, vials, syringes, or other suitable components of a kit.

Microfluidic Device

In one aspect, the invention provides a novel circulating tumor cell (CTC-specific) isolation device that enables the identification and capture of viable CTCs for detection, propagation and molecular characterization purposes. Although not so limited, the present invention is particularly well suited for identification and capture of viable CTCs derived from peripheral blood samples. The invention provides for the selected tagging of enriched CTCs with an extracellular, detectable (e.g., fluorescent) epitope via adenoviral transduction and the use of easy-release, biotinylated primary antibodies against this epitope to mediate CTC immunocapture and isolation by means of a biotin-binding protein coated microfluidic device. Cancer cell-specific tagging is achieved as described herein, e.g., by exposing an enriched CTC sample, prepared by liquid density separation of a whole blood sample, to an adenovirus that delivers a specific episomal marker.

The selectivity of the CTC tagging is conferred by the use of the adenoviral vector system described in this specification. However, alternative systems may be used with the device of the invention. For example, a fusion protein composed of epithelial cell adhesion molecule (EpCAM) and green fluorescent protein (GFP) may be delivered via an adenoviral vector for capture in the CTC microfluidic device of the invention.

Existing (prior art) methods for capture and/or detection of CTCs depend on the endogenous expression of specific proteins typically associated with epithelial cells. These proteins include EpCAM and cytokeratins (Ck). However, consideration differences in expression profile of these proteins may exist between CTC samples or even among tumor cells in a single sample. This limits the population of CTCs that can be captured and/or detected by these methods to only those cells expressing these specific epithelial cell proteins. Furthermore, due to the process known as Epithelial-Mesenchymal-Transition (EMT), EpCAM expression may be down regulated or absent in CTCs. Without wishing to be bound by theory, it is believed that by selectively tagging CTCs via an adenoviral-delivered exogenous epitope as described above, the method and device of the invention extends the phenotypic range of CTC populations that can be captured and/or detected and simplifies the process of immunocapture and identification of these cells. Immunocapture of tagged CTCs is accomplished by incubating cells with easy-release, biotinylated antibodies against the tagging epitope, then by flowing them through a microfluidic device of the invention containing biotin-binding protein (NeutraAviden™ deglycosylated avidin protein)-coated microcolumns. The incubation step with the early-release, biotinylated antibody allows the cell surface of CTCs to be bound with biotin molecules that are used to capture these cells with the microfluidic device through biotin-avidin chemistry. The microfluidic device of the invention is described below. The device contains four capture channels, each containing an array of microcolumns of various shapes that include cylindrical, oval and a combination of triangular and chevron-like structures arranged in different orientations.

In one embodiment, easy-release, biotinylated antibodies are used to mediate the capture of CTCs, including the EZ-Link® NHS-SS-PEG4-Biotin labeling system (Pierce, Thermo Scientific) and the DSB-X™ Biotin labeling system (Molecular Probes, Invitrogen). The EZ-Link® NHS-SS-PEG4-Biotin labeling system allows labeled antibodies to be captured with biotin molecules containing a flexible spacer arm with a reducible disulfide bond. The DSB-X™ Biotin labeling system allows a precursor of biotin, desthiobiotin, to be incorporated. This precursor binds biotin-binding proteins and can be readily displaced by excess D-biotin. Still other suitable easy-release biotinylated antibodies may be selected or designed.

Without wishing to be bound by theory, this easy-release system is believed to be advantageous over the prior art methods because the prior art chemical and physical methods required to overcome the strong binding forces used to immobilize CTCs onto micro-columns of a microfluidic device are known in the art to adversely affect cell viability and function.

Once captured and visualized (e.g., by observing fluorescence), CTCs are imaged, identified and enumerated in a transparent PDMS microfluidic device using a suitable detection system, e.g., a sensitive fluorescent microscope (Eclipse TE2000-U, Nikon Corp), and automated stage and an image analysis program (e.g., Image-Pro Plus 7.0, Media Cybernetics, Rockville, Md.).

CTCs are immunocaptured within the microfluidic device. Immunocapture of CTCs using the microfluidic device is achieved by a series of steps. First, the enriched cell sample is exposed the replication-deficient adenovirus described within this document. This allows for the selective labeling of CTCs in the sample with a cell-surface, fluorescent fusion protein also described herein. Once CTCs are labeled, as monitored by fluorescence intensity, the enriched sample is incubated with a biotinylated antibody that recognizes the fluorescent fusion protein expressed by CTCs and bind to these proteins at the surface of CTCs. After decorating CTCs with biotinylated antibody, enriched sample is flowed through the microfluidic device. Since the capture channels, including the microcolumns within them, have been functionalized with a biotin-binding protein (e.g., streptavidin), flowing cells bound with biotinylated antibody, mostly CTCs, get trapped at the surfaces of the channels. This trapping event is mediated by the strong covalent bond formed between the biotin-binding protein immobilized to the channel's surface and the biotin moiety in the antibody attached to the flowing CTC. Finally, loosely trapped cells are removed from the capture channels by washing them away. Hence, only cells trapped via immunocapture remain immobilized in the channels of the microfluidic device.

After immunocapturing CTCs are released by exposing them to either tris(2-carboxyethyl)phosphine (TCEP), a water-soluble, thiol-free reducing agent or to d-biotin depending on the biotin labeling system used and by driving them out of the microfluidic device and into a collection microcentrifuge tube by laminar flow. Both TCEP and D-biotin preserve cell viability and their phenotypic characteristics. By using easy-release, biotinylated antibodies to immunocapture CTCs, this novel methodology makes possible the favorable release of captured CTCs from the microfluidic device for effective cell culture propagation and molecular characterization of the cells.

A microfluidic device is described herein which facilitates the efficient isolation of circulating tumor cells (CTCs) from an enriched sample. This device is particularly well suited for use with the method of the invention. However, it may also be adapted for use in other methods as well.

A microfluidic device for isolating circulating tumor cells from a sample is composed of an optically clear substrate having bound thereto at least four capture channels. In one embodiment, the substrate is glass and may be e.g., a standard microscope slide. Microscope slides are usually made of glass, such as soda lime glass or borosilicate glass, but specialty plastics are also used. Fused quartz slides are often used when ultraviolet transparency is important, e.g. in fluorescence microscopy. A standard glass slide typically measures about 75 mm by 25 mm (3" by 1") and is about 1 mm thick. However, a range of other sizes are available for various special purposes, such as 75×50 mm, 46×27 mm, and 48×28 mm for thin sections. Slides are usually made of common glass and their edges are often finely ground or polished.

A microfluidic device contains at least four, 6, 8, or more capture channels comprising an arrangement of different-shaped microcolumns. These microcolumns include one or more cylindric, elliptical, triangular and chevron-like microcolumn capture units. Each of the capture chambers comprise at least floor and sidewall surfaces which have a capture agent for circulating tumor cells in the sample. The device further contains an inlet reservoir and an outlet reservoir and distribution channels (5) which transport the flow of a sample from the inlet reservoir over the length of the capture channels to the outlet reservoir.

The number of channels may be varied, e.g., from 4 up to about 8 channels could be incorporated into the device based on size limits for the device and the channels themselves. The arrangement of the capture channels may vary from that of FIG. 2. For example, when the units are arranged in horizontal rows (perpendicular to the channel's walls), they can also shift after every other or every third row. They can also be shifted vertically by varying the distance between neighboring rows every other or every third rows. Besides being arranged in horizontal rows, these units could also be organized in vertical rows (parallel to channel's walls) and be shifted either horizontally or vertically as described for the horizontal rows. Units could also be arranged randomly throughout the channel. Alternatively, the channels may be fragmented into four shorter structures, each containing the different microstructures, or connected in series to make up the full length of a single channel presented in FIG. 2.

The desired measurements and patterns for the distribution of any of the capture units, microcolumns and channels described herein are achieved by getting a photomask printed with this specific measurements and design. This design (along with measurements) is created using a software for Computer-Aid-Design (CAD) such as AutoCAD®. The software file containing the design patterns of the invention are used to make print the photomask a described below. The photomask is used to make the SU-8 mold during the PDMS double casting prototyping by thermal aging of PDMS.

Figure 2:
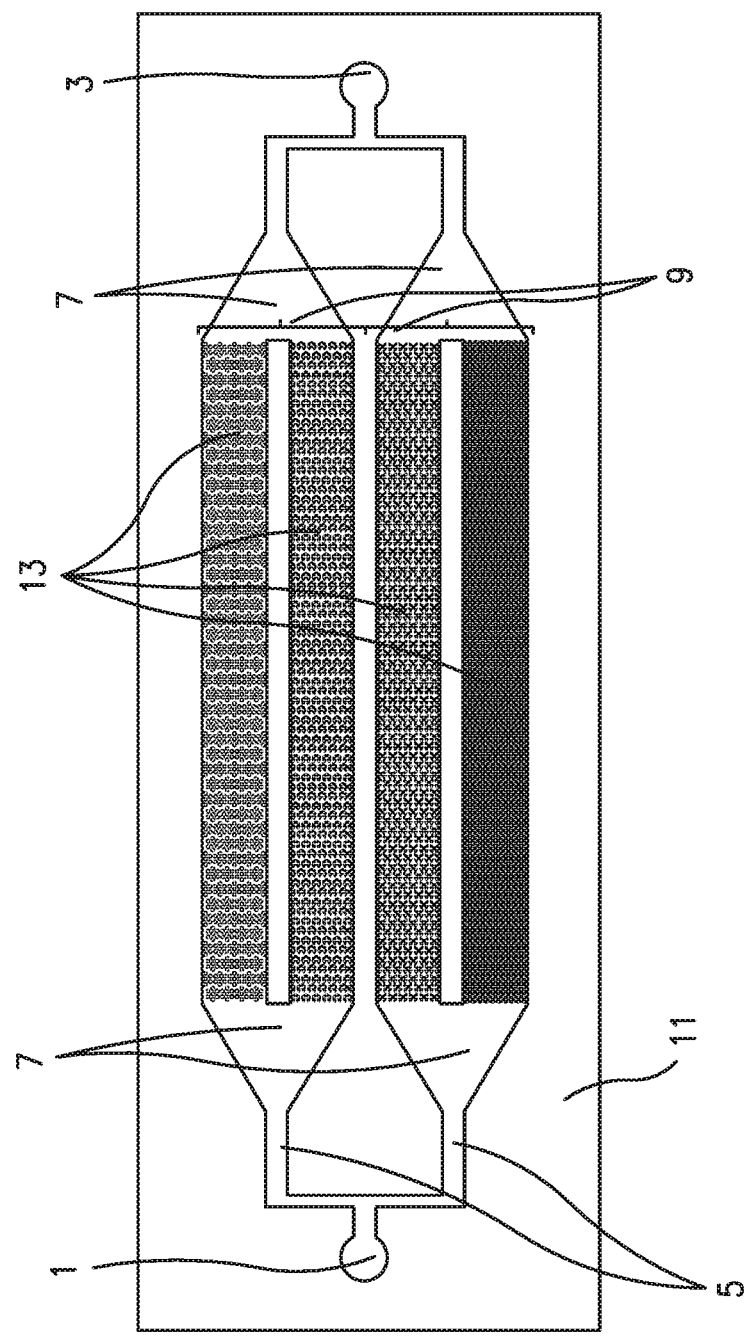
FIG. 2 is a schematic representation of a microfluidic device of the invention. As illustrated, this device has four capture channels arranged in parallel with an array of microcolumns with different geometrical shapes between channels. These channels are connected to an inlet and an outlet reservoir through a system of distribution channels that distribute facilitates the flow of sample into and out of the capture channels.
Figure 4B:
FIG. 4A-FIG. 4C provides schematic diagrams of the device of FIG. 2.
Figure 4C:
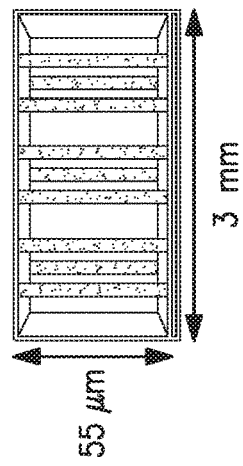
Figure 4A:
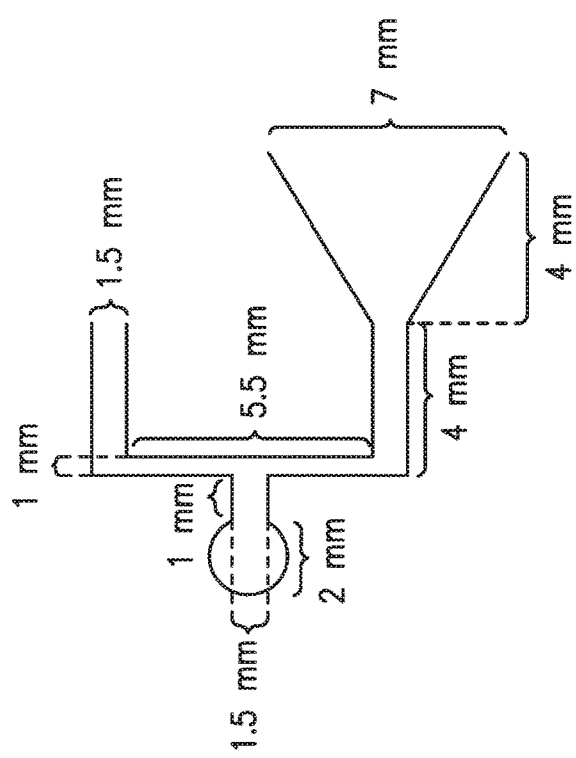
Figure 6A:
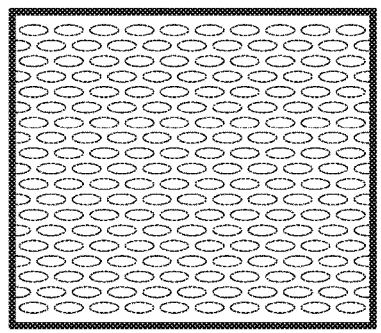
FIGS. 6A-6C provide enlarged views of the elliptical microcolumns in one of the channels of the device of FIG. 2.
Figure 6B:
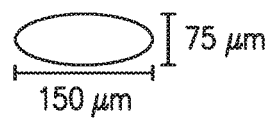
Figure 6C:
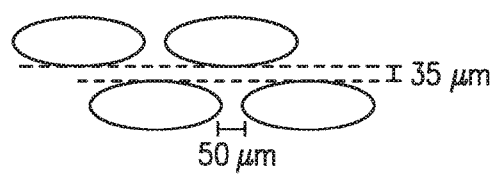
Figure 7A:
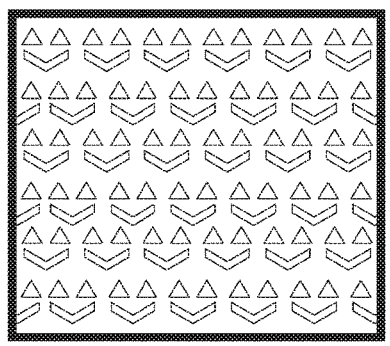
FIGS. 7A-7D provides enlarged views of one of the microcolumns of the device of FIG. 2, which combines triangular and chevron-like microcolumns.
Figure 7B:
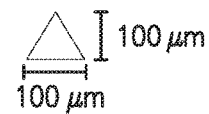
Figure 7C:
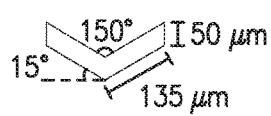
Figure 7D:
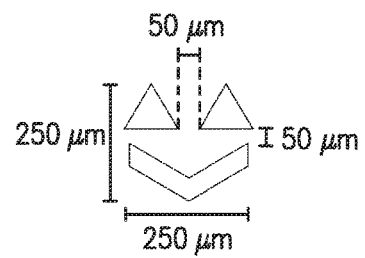
Figure 8A:
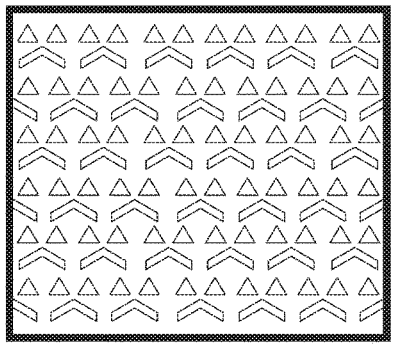
FIGS. 8A-8C provides enlarged views of a second microcolumns of the device of FIG. 2 which combines triangular and chevron-like microcolumns.
Figure 8B:
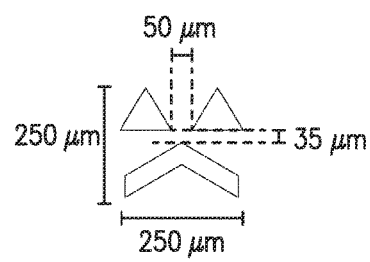
Figure 8C:
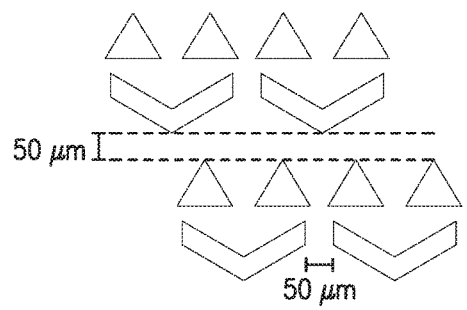

With reference to FIG. 2, the device may have four capture channels (9). The capture channels are connected to an inlet (1) and an outlet (3) by a system of distribution channels (5). Each capture channel 9 contains an array of different-shaped microcolumns 13 that span the height of the channel. These microcolumns 13 are organized within the channel in capture units that consist of either a set of hexagonally arranged cylindrical microcolumns (FIG. 5A-D), a set of combined triangular and chevron-like microcolumns (FIGS. 7A-8C) or individual elliptical microcolumns (FIGS. 6A-6D). Additionally, the capture channels and the microstructures within them are chemically functionalized with the biotin-binding protein avidin or its analogs for mediating the isolation of CTCs decorated with biotinylated antibodies against specific cell surface epitopes prior to their introduction to the device. The different capture units within the channels are designed to disrupt the linear path of flowing cells and to increase capture surface area; thus, maximizing the interaction between biotinylated antibody-coated cells and the capturing agent. This approach to CTC isolation takes advantage of the rapid binding kinetics characteristic of the biotin-avidin interaction; therefore, lowering the duration of cell to surface/microcolumn contact required to ensure cell capture. Furthermore, this approach facilitates the use of immunologic cocktails, which could help capture CTCs based on the presence of different cell surface epitopes. This reduces or eliminates the dependency of CTC capture on the expression of a single epitope.

The microfluidic device is designed with a system of distribution channels that connect an inlet reservoir 1 to the capture channels for sample introduction and the capture channels to an outlet reservoir 3 for sample removal. Suitably, the device is made of polydimethylsiloxane (PDMS) cast bonded to a glass slide 11 and FIGS. 3F-3I. Based on physical properties, including transparency and porosity (for gas exchange) and biocompatibility, PDMS is particularly well suited as the elastomer. However, PMMA (poly(methyl methacrylate) may be selected and applied to the substrate using methods such as hot-embossing rather than photolithography like PDMS. Engraved on the PDMS cast is the pattern of grooves and microcolumns that will form the characteristic channel system of the device upon bonding to the glass slide (FIG. 3D-FIG. 3G). The PDMS double casting prototyping by PDMS thermal aging is the process by which the pattern of grooves and microcolumns is engraved on PDMS.

In one aspect of the device, the PDMS cast is produced by double casting a prototype combined with thermal aging of PDMS (FIG. 3E). This process facilitates the appropriate replica of the microcolumns embedded in the capture channel grooves. In this process, an SU-8 master containing the pattern for the channel grooves and microstructures is produced by photolithography (FIG. 3E). Briefly, the designed pattern of channels and microstructures for our device is transfer onto a photomask. This mask is a glass plate containing the designed pattern printed on its surface using an opaque material (chrome). The photomask is then brought into contact with a thin film (~55 μm) of SU-8 (negative photosensitive substrate) previously deposited onto a silicon wafer. UV light is shown through the mask and onto the SU-8 film. Since SU-8 is a negative photoresist, areas exposed to UV-light get crosslinked and solidify, while unexposed areas remain soluble. Unexposed SU-8 areas are then removed by washing the thin film with a developing solution. Thus, upon completion of the photolithography process, the desired pattern of grooves and microstructures is engraved on the SU-8 film, which is then used as a mold to transfer this pattern onto the first PDMS replica (FIG. 3D).

Polydimethylsiloxane (PDMS) casting is achieved by mixing the PDMS pre-polymer with curing agent at a weight ratio of about 1:5 to about 1:15, or about 1:8 to about 1:10, or about 1:9 (curing agent: base) and curing these mixture at about 60 C for about 24 hours to about 80 C for about 2 to 4 hours. Typically, higher temperatures within this range are associated with the shorter curing times and the lower temperatures with longer curing times, e.g., about 70° C. for about 3 to 4 hours, about 80° C. for about 2 to 3 hrs or about 65° C. overnight (~16 hrs). The pre-polymer and curing agent are available commercially, e.g., as SYLGARD 184 silicone elastomer base & dimethyl, methylhydrogen siloxane curing agent from Dow Corning, This pre-polymer to curing agent weight ratio allows for fabrication of microstructures with the desired elasticity to avoid damaging the patterned microcolumns during demolding of PDMS casts. The aforementioned weight ratio and curing conditions are used during both PDMS castings steps. Then negative PDMS replica resulting from the first casting process is then thermally aged (FIG. 3G) at about 80° C. for at least about 72 hours PDMS slabs can alternatively be thermally aged at about 100° C. for about 48 hrs. Other variations in temperature and time within these two ranges will be apparent to one of skill in the art. Finally, the thermally aged negative PDMS replica serves as mold to cast a second PDMS replica with positive orientation (FIG. 3H).

In another aspect of the device, microfluidic units are fabricated by bonding a positive PDMS cast or replica to a glass slide after surface activation of both components by plasma edging (FIG. 3I). Bonded microfluidic units have width and length dimensions similar to a typical microscope slide, 25 and 75 mm respectively. The height of the device varies depending on the volume of PDMS used during the second casting step.

In one aspect of the device, the inlet and outlet reservoirs used have a diameter of 2 mm. The inlet reservoir is connected to the capture channels entry side by distribution channels 55 µm in height. As illustrated in FIG. 2, distribution channels may be composed of a short, vertical channel. In one embodiment, such a channel is about 1 mm in length and about 1.5 mm in width. This channel connects to a long perpendicular channel 8.5 mm in length and 1 mm in width that splits the sample into two sample delivery sections. Each delivery section distributes sample to two of the four capture channels through a vertical channel 4 mm in length and 1.5 mm in width. This vertical channel opens about 45° on each side to gradually increase the cross-sectional flow area and introduce the sample into both capture channels included in the specific delivery section. A similar system of distribution channels facilitates the transport of sample from the exit side of the capture channels to the outlet reservoir for sample removal.

In yet another aspect of the device, capture channels are about 44 mm in length, about 3 mm in width and about 50 microns (µm) to about 70 microns height (depth). In one embodiment, the channels are about 55 µm. Each capture channel comprises an array of different-shaped microcolumns that include cylindrical, elliptical and a combination of triangular and chevron-like columns arranged in different orientations.

In one aspect of the device, the cylindrical microcolumns included in one of the channels have a diameter of about 100 µm to about 200 µm and a height of about 50 µm to about 70 µm. In one embodiment, the channels have a diameter of about 100 µm and a height of about 55 µm. The cylindrical microcolumns are arranged in hexagonal-shaped units which units about 340 µm to about 700 µm in width and length. In one embodiment, the hexagonal-shaped units are about 370 µm in width and length. Each hexagonal unit is comprised of seven individual cylindrical microcolumns distributed so that six microcolumns sit at each vertex of the hexagon and one microcolumn sits at the center of the hexagon. These units may be arranged in rows which are horizontally or vertically located relative to the substrate. Typically, these rows of hexagonal-shaped units are shifted horizontally or vertically after each two to three rows. However, other shifts may be selected, or the hexagonal-shaped units may be randomly located. Individual cylindrical microcolumns are separated about 20 µm to about 50 µm, or about 35 µm from neighboring microcolumns within a hexagonal unit. Additionally, individual hexagonal units are separated by about 35 µm to about 75 µm, or about 50 µm within each row of units and each hexagonal unit is shifted about 35 µm to about 75 µm, or about 60 µm horizontally after every two to three rows. When in vertical rows, similar shifts may be applied.

In another aspect of the device, two of the capture channels include capture units that combine triangular and chevron-like microcolumns in height. These capture units may range in size from about 210 µm to about 700 µm. Each of these unique capture units is comprised of two parallel triangular columns with a base and height (depth) of about 100 to about 325 µm each and a separation from about 25 µm to about 50 µm between them. A chevron-like column placed at the base of the parallel triangular microcolumns complements these capture units. These chevron-like columns are about 225 µm to about 700 µm, or about 250 µm in length, about 20 µm to about 50 µm in width and have an aperture angle of about 145° to about 165°, or about 150° aperture angle. In addition, the orientation of the chevron-like columns serves to differentiate the capture units on each of the two channels containing this array. Capture units in which the chevron-like microcolumn points toward the base of the parallel triangular columns, the minimum separation between chevron-like and triangular columns is about 20 µm to about 50 µm, or about 35 µm, and this type of capture unit is about 200 µm to about 700 µm, or about 210 µm in length and about 200 µm to about 700 µm, or about 250 µm in width. The combined units where the chevron-like column has the opposite orientation, that is it points away from the base of triangular columns, the minimum separation between the chevron-like and triangular columns is about 20 µm to about 50 µm and the complete capture unit is 200 µm to about 700 µm in length and width. Each of these types of capture units may be separated from neighboring individual units within and between rows, and are shifted 200 µm horizontally or vertically every row, every other row, or the units may be located randomly.

As with the hexagonal shaped capture units composed of cylindrical columns, the distances from unit to unit within a row or from row to row are not critical. These capture units can also be arranged in horizontal rows (perpendicular to channel's walls) and shift horizontally but after every other or every third row. They can also be shifted vertically by varying the distance between neighboring rows every other or every third rows. Besides being arranged in horizontal rows, these units could also be organized in vertical rows (parallel to channel's walls) and be shifted either horizontally or vertically as described for the horizontal rows. Finally, units could also be arranged randomly throughout the channel. In one aspect of the device, elliptical microcolumns embedded in the last of the four channels have dimensions of about 100 µm to about 250 µm, or about 150 µm and about 50 µm to about 150 µm for major and minor axes and height. In one embodiment, the major and minor axes are about 75 µm or about 55 µm respectively. The distance between single units and between rows of units may be varied. In one example, each elliptical microcolumns is separated by about 50 µm to about 70 µm from its neighboring columns within a row and about 50 µm to about 70 µm, or about 35 µm from neighboring columns between rows. Elliptical microcolumns shift from about 100 µm to about 250 μm horizontally or vertically after every row, or every other row, when arranged in rows and not randomly spaced in the channel.

Once produced, the device can be used to detect circulating tumor cells as described herein. Alternatively, the device may be adapted for use in other methods.

In one aspect, sample suspected of containing circulating tumor cells is introduced into the inlet reservoir of the device. In one embodiment, sample suspected of containing circulating tumor cells is introduced into the device via a flexible tube (e.g., Tygon® tubing, St. Gobain), which connects the source containing the sample (e.g., a metal hub blunt point needle fixed to a syringe) to the inlet reservoir of the device. Similar tubing is also attached to the outlet reservoir for outflow into a waste or collection container, typically a microcentrifuge tube. The sample is injected into the device with a continuous flow at rates ranging from about 10 μl/min to about 30 μl/min. Once the sample has been injected, the channels are washed from two to three times with a suitable solution (e.g., a phosphate buffered saline (PBS)) with a continuous flow at rates ranging from about 50 μl/min to 200 μl/min. In one embodiment, a syringe pump or an equivalent means capable of producing flow rates in the μl/min range is used to control the flow for sample injection and washing steps. A suitable amount of the sample is permitted to flow through the distribution channel into the vertical channels and all surfaces of each capture channel come in contact with the flowing sample. The surfaces, which include the floor, ceiling, and sidewalls of the capture chambers of the microcolumns within each channel, are coated with a suitable capture agent. For use in connection with circulating tumor cells, the capture agent may be a biotin-binding agent selected from a group of biotin-binding proteins including avidin, streptavidin and deglycosylated avidin (such as NeutrAvidin™).

The capture agent may be bound directly or indirectly to the surface. For example, in one embodiment, the capture agent is immobilized to all capture surfaces of each channel via a cross-linker. Suitable cross-linkers may include N-[γ-maleimidobutyryloxy]succinimide ester (GMBS), which is used to covalently attach the capture agent channel surfaces. Covalent attachment of the capture agent is facilitated by the N-hydroxysuccinimide ester moiety of GMBS. In another embodiment, the capture agent is covalently attached to all capture surfaces of each channel through the maleimide moiety of the cross-linker GMBS. Prior silanization of capture surfaces is required for the covalent attachment of the cross-linker. The silanization agent (3-mercaptopropyl) trimethoxysilane may be used for surface activation on this device. Still other capture agents may be selected for use in the present invention.

The words "comprise", "comprises", "comprising", "contain", "contains" and "containing" are to be interpreted inclusively rather than exclusively. The works "consist", "consisting", and its variants, are to be interpreted exclusively, rather than inclusively.

As used herein in reference to numeric values provided herein, the term "about" may indicate a variability of as much as 10% unless otherwise specified.

The following examples are illustrative of embodiments of the invention and do not limit the scope of the invention.

EXAMPLE 1

Example 1 describes preparation and process of patient-derived blood samples for CTC Analysis, i.e., CTC-enrichment which is optionally used in conjunction with the non-lytic adenoviral system for detection of circulating CTC.

A. Initial Sample Processing

After discarding initial two 6 mL tube collections to avoid contamination by epithelial stem cells, peripheral blood samples will be obtained in two 6-mL sodium heparin green top tubes and immediately placed on ice. Blood will be drawn until vacuum ends, with ideal total blood volume of at least 10 mL. Specimens will be processed within two hours of collection in compliance with CTC enrichment protocol manufacturer recommendations.

B. CTC Enrichment

Following combination of 10 mL sterile phosphate buffered saline in conical with blood collection, mixture will be chilled on ice for 15 minutes. Meticulous care will be exercised to introduce blood solution to OncoQuick tube, prior to centrifugation for 20 minutes at 1500 RCF.

Harvesting of the CTC-enriched layer consists of upper plasma layer aspiration to 5 mL above the demarcated interphase layer. The remaining solution overlying the porous barrier will be sterilely extracted and placed in a separate 50 mL conical containing 30 mL sterile wash buffer (0.5% Bovine Serum Albumin in 1×PBS). 10 additional mL wash buffer will be introduced to Onco-quick tube to collect residual CTCs adhering to conical or porous barrier surfaces, before adding to the separate 50 mL conical, bringing total CTC enriched dilute solution to 50 mL total volume. Centrifugation of this conical will be conducted for 10 minutes at 250 RCF. Aspiration to 5 mL gradation will be carefully performed, prior to employment of P-1000 mcL pipettor until 500 mcl CTC enriched cell pellet suspension remains. Following incubation in 37° C. water bath, 1000 mcl cell culture media (DMEM, 10% fetal bovine serum, 1% Penicillin/Streptomycin) will be introduced to allow cell pellet re-suspension, prior to aliquot of 750 mcl into each of two poly-D-lysine chamber wells.

B. Assay:

CTC Assay Protocol: Materials and Methods

Materials:
- Gradient centrifuge tube (e.g. Oncoquick tube)
- 50 mL propylene centrifugation tube
- Centrifuge capable of generation 1600 RCT at 4° C. with swinging bucket rotor and tube carriers/adapters for 30×115 mm tube size
- Disposable serological pipettes
- Washing buffer: 1× phosphate buffered saline (PBS)+ 0.5% w/v bovine serum albumin (BSA)
- Gloves appropriate for protection vs bloodborne infections
- Blood sample
- Poly d lysine coated chamber wells and 6 cm petri dish 1. Introducing Patient Blood Sample into Tube (See, e.g., FIG. 1A)
- To minimize further possible loss of tumor cells due to non-specific adsorption to dry plastic surfaces, prewet all dry surfaces with washing buffer by simply pipetting up and down once or rinsing once to prewet all fresh serological pipettes or 50 mL tubes respectively
- Do not introduce blood right onto porous barrier since this can result in mix up the separation medium with blood thus decreasing separation quality
- Slightly incline the oncoquick tube and introduce blood slowly down side of tube Preparation
  Precool centrifuge to 4° C.
  Obtain ice bucket filled with ice
  Precool oncoquick tubes and blood specimens for 10-15 min on ice (important to perform this procedure within 2 hours of blood draw)
  Ensure separation medium (blue) is completed in the lower compartment and if not-->spin oncoquick tube to bring separation medium back into lower compartment
  If oncoquick solution is higher than porous line-->centrifuge on RCF slow 1500 RCT for 4 min
  Obtain mask, gown, gloves
  Blood sample contained in 2 separate 6 mL tubes containing sodium heparin
  Spray down blood sample tubes with EtOH
Enrichment: washing steps can be performed at RT if convenient
Prewash conical with wash buffer (add 25 mL 0.5% BSA in PBS and remove)
Aliquot:
Sporogon into 50 mL conical
0.5% BSA in PBS (wash buffer used to wash any pipette that will make contact with cells to prevent adherence to conical) into 50 mL conical
Sterile PBS into 50 mL conical
Obtain 10 mL pipette and wash (×1) inside of 10 mL pipette with wash buffer
Pipet 10 mL sterile PBS and place in 50 mL conical
Obtain 10 mL pipet and wash with wash buffer
Invert blood sample×5 and repeat with collection of all blood from both tubes into one 10 mL pipet
Make note of total blood volume (around 10 mL)
Add blood sample (approximately 5 mL usually from each blood tube sample) to 10 mL sterile PBS-->pipet×5 for adequate mix ensuring not to advance higher than blood line
Wash pipet with sporogon (×2) and discard
Incubate oncoquick tubes and blood specimens on ice for 15 minutes
Wash 25 mL pipette with wash buffer (×1)-->pipet blood-->obtain all blood in pipette and carefully/slowly introduce in side of oncoquick tube
Fill the cooled whole blood (15-30 mL) gently into upper compartment without disturbing medium underneath porous barrier via introducing to side of oncoquick tube
Note: use 25 mL pipet to obtain first collection then switch to 2 mL pipet to obtain remaining blood in conical to ensure least amount of remnant cells
With anti-viral solution (e.g., Spor-Gon) disinfect the used pipette and the remaining conicals
2. Centrifugation and Cell Separation (See, e.g. FIG. 1B)
Spin blood filled OncoQuick™ tube at 1500×g (aka RCF) and 4 C for 20 min in a swing bucket rotor with slow acceleration and no brake
After centrifugation, tumor cells will be in interphase between upper plasma (yellow/brown) and lower separation medium (blue). Usually this cell fraction is not visible.
If interphase is at 20 or lower-->aspirate to 25, but if interphase layer exceeds 20 mark then aspirate to 5 mL above interphase layer
Place 30 mL wash buffer in fresh conical/centrifugation tube 3. Removal of CTC-Enriched Cell Layer (See, e.g., FIG. 1C)
  The entire remaining liquid volume above the porous barrier can be collected with sterile serological 10 mL pipette and transferred to mix with 30 mL wash buffer
  Remove top of the layer down to prevent most cells from sticking to porous barrier
  Carefully rinse inner tube wall and the surface of the porous barrier of the emptied oncoquick tube with approximately 10 mL washing buffer to collect cells eventually adhering to these surfaces
  Add them to centrifuge tube already containing transferred liquid volume and bring volume to a total 50 mL using wash buffer (had 10 mL sample and add 30 mL wash buffer, make total 50 mL by adding 10 mL wash buffer to oncoquick to retrieve remaining cells)
  Mix suspension by gently inverting tube 5 times
  Pellet the cells at 250×g (aka RCF) for 10 min
  Obtain 2 mL media (10% FBS, 1% Pen Strep) and place in water bath warmer
  Gently aspirate about 49.5 mL supernatant without disturbing cell pellet and leave the pellet in the remaining 500 microL of washing buffer
  Perform this by aspirating to 5 mL mark, then obtain P1000 pipet and aspirate 1 mL×4 then an additional 500 microL (each time with new pipet tips)
  Add 1 mL culture media (10% FBS, 1% Pen Strep)
3. Moving CTCs to Chamber Slide for Immunofluorescent Microscopy (See, e.g., FIG. 1D)
  Obtain new tip and set to 750 microL-->add 750 microL (obtained from middle of solution) to each well in 2 poly D lysine coated chamber slide wells
  Divide remaining fraction between both wells (do one drop at a time)
4. Adding Vector (See, e.g., FIG. 1E)
  Add 495 microL of media to 5 microL virus aliquot in aliquot labeled "V"
  Pipet up and down 5 times to mix
  "1:100"
    Obtain new pipet tip set to 50 microL and obtain 50 microL solution from "V", adding to new aliquot labeled "1:100"
    Add 450 microL media (10% FBS, 1% Pen Strep) to separate aliquot labeled 1:100
    Mix thoroughly×5
    Put 50 microL of diluted OBP 401 in 1:100 well
  Using new gloves, remove chamber well from under hood and place in petri dish, covering with clean gloved hand
  Incubate chamber well in 37° C. incubator
F. Method for Verification and Quantification of CTCs (See, e.g., FIG. 1F)
CTCs may be imaged, quantitated, and characterized. Fluorescent microscopy imaging can be used as follows. At 24 hours post transfection/infection, 100×tiled fluorescent images of each chamber well will be obtained, prior to fixation to avoid potential loss of non poly-d-Lysine adherent, circulating tumor cells. Images will be saved and subsequent analysis per semi-automated computer software will be performed to allow sorting, capturing and filtering of CTC. Enumeration will then be employed per established parameters (Fluorescent intensity, cell area, cell diameter) and algorithm. Following imaging, chamber wells will be fixed with 10% neutral buffered formalin solution. Counterstaining can then be performed to qualitatively assess isolated circulating tumor cells.

EXAMPLE 2

A Telomerase-Based Single-Adenovirus Assay Detects Circulating Tumor Cells

Human glioblastoma-derived U251 cells were obtained from the American Type Culture Collection, ECACC catalogue number: 09063001 and suspended in Dulbecco's modified Eagle's medium (DMEM, Invitrogen, Carlsbad, Calif.) supplemented with 10% fetal bovine serum (FBS, Invitrogen, Carlsbad, Calif.) and 1.0% penicillin-streptomycin at 37° C. in an atmosphere of 5% $CO_2$. Cells were seeded on 8 well Poly-d-lysine chamber slides at a pre-determined optimal density of $5 \times 10^3$ cells/well (enumeration provided via Nexcelom Biosciences' Cellometer in duplicate) just prior to viral infection.

A non-lytic adenoviral particle according to the invention was constructed using conventional techniques, e.g., as described on http://www.med.upenn.edu/gtp/vectorcore/production.shtml. The source of adenoviral capsid and genomic sequences was human adenovirus 5 (Ad5).

The Human TERT promoter was synthesized based on the sequences published previously (Kawashima, T, et al. Telomerase-Specific Replication-Selective Virotherapy for Human Cancer. Clin Cancer Res., Jan. 1, 2004 10; 285). The transgene expression cassette containing the Human TERT promoter was first inserted in pShuttle plasmid and flanked in between 2 meganuclease enzyme sites, I-CeuI and PI-SceI. The expression cassette was then excised by I-CeuI and PI-SceI digestion and sub-cloned into adenovirus backbone plasmid (pH5' 0.040.CMV.A1AT from Penn Vector Core) by replacing the fragment flanked by the same enzymes. The recombinant adenoviral vector is generated by treating the plasmid with PacI to release both Inverted Terminal Repeat sequences (ITRs) of the adenoviral vector genome, followed by transfection (e.g. 5 μgs per 25 cms flask) and rescue in HEK293 cells. The vectors were expanded and purified by density gradient centrifugation from the lysate harvested from infected 293 cells via by 3 cycles of freeze-thawing. The physical particle titer of adenoviral vectors was determined using absorbance readings at 260 nm via a spectrophotometer. The vectors were further characterized by genome DNA structure analysis, infectivity assay and replication competent adenovirus (RCA) assay. See, e.g., http://www.med.upenn.edu/gtp/vectorcore/quality_control.shtml.

In the resulting construct, termed Ad.hTert.eGFP contains deletions in the wild-type E1 region (E1a and E1b) and the E3 region of the Ad5, rendering it non-lytic. The construct further contains an exogenous expression cassette containing, from 5' to 3' the hTERT promoter (376 bp+5' UTR), eGFP gene, a polyA-Woodchuck hepatitis virus post-transcriptional regulation element (WPRE), and a rabbit beta-globulin poly A. Use of the hTERT promoter makes the expression of the enhanced green fluorescent protein dependent upon the presence of telomerase, which is indicative of the presence of circulating tumor cells. This adenovirus does not contain any insert in the E3-deleted region, and with the exception of the E1-deletion and E3-deletion retains other adenoviral genomic regions necessary for to package the genomic sequences into the adenoviral capsid and form the replication-defective adenoviral particle. The techniques used to generate the vector are well known to those of skill in the art.

Following titration of the cells into the wells, Ad.hTert.eGFP viral particles of non-lytic telomerase-specific adenoviral vector were added to the cells at various concentrations ($5.9 \times 10^7$, $5.9 \times 10^8$, $2.95 \times 10^8$, $2.95 \times 10^9$, $1.1 \times 10^{10}$ viral particles (also termed genome copies)), which are thereafter incubated at 37° C. under 5% $CO_2$ Expression levels of eGFP protein in the cells are tested at 24, 28, 72, 96, and 120 hours. In order to maintain cell viability during this time, media is replaced as needed.

Fluorescent cells were detected via a PlanNeofluor lens objective mounted on a Nikon TE-2000 microscope equipped with epifluorescence optics. The epifluorescent images were captured with a Hammamatsu charge-coupled-device camera that was controlled with IP LabSpectrum software, thus detecting cells expressing GFP.

These results showed that a dilution of 1:100 was optimal, showing approximately 3 billion viral particles and good imaging at 48 hours. However, this system using the non-lytic telomerase-specific adenoviral vector still showed acceptable results over all time points and at all concentrations.

EXAMPLE 3

A Telomerase-Based Two Adenovirus Assay Detects Circulating Tumor Cells

Human glioma cells U251 and suspended in a suitable as described in Example 2 above. Cells were seeded on 8 well Poly-d-lysine chamber slides at a pre-determined optimal density of $5 \times 10^3$ cells/well (enumeration provided via Nexcelom Biosciences' Cellometer in duplicate) just prior to viral infection.

A first non-lytic adenoviral particle according to the invention was constructed and is termed hTert.Cre. The source of adenoviral capsid and genomic sequences was human adenovirus 5 (Ad5). In the resulting construct, the wild-type E1 region (E1a and E1b) and the E3 region of the Ad5 are deleted. An exogenous expression cassette containing, from 5' to 3' the hTERT promoter, the Cre recombinases coding sequence, a polyA-Woodchuck hepatitis virus post-transcriptional regulation element (WPRE). This adenovirus does not contain any insert in the E3-deleted region, and with the exception of the E1-deletion and E3-deletion retains other adenoviral genomic regions necessary for to package the genomic sequences into the adenoviral capsid and form the replication-defective adenoviral particle. A second adenoviral particle, termed Ad.CB.Flex.eGFP was also constructed. This construct contains an E1- and E3-deletion, and an exogenous expression cassette in the site of the E1 deletion. The expression cassette contains a CAGS promoter, a loxP site, an inverted eGFP gene-polyAWPRE, and a second loxP sequence. The CAGS promoter is a ubiquitous strong promoter/enhancers composed of the chicken β-actin promoter with human cytomegalovirus immediate early (CMVIE) enhancer. The techniques used to generate the vector are well known to those of skill in the art. In this two-vector system, telomerase-specific expression of the Cre protein caused the inverted reporter gene to flip and expression the fluorescent protein. This system is self-amplifying because the CAGS promoter is constitutive.

Following titration of the cells into the wells, the two non-lytic telomerase-specific adenoviral vectors were added to the cells at $1.14 \times 10^9$ combined viral particles or $1.14 \times 10^8$ combined viral particles (genome copies or GC). Because this system is self-amplifying, the ration of Ad.hTert.Cre to Ad.CB7.Flex.eGFP is 2:1. Following infection, the cells are incubated at 37° C. under 5% $CO_2$. Expression levels of eGFP protein in the cells were tested at 24, 28, 72, 96, and 120 hours. In order to maintain cell viability during this time, media was replaced as needed.

These results show that the combined virus system, while expression time was somewhat slower than the single virus system of Example 2, higher expression levels were obtained.

However, this system using this dual non-lytic telomerase-specific adenoviral vector system, acceptable results were observed.

EXAMPLE 4

Microfluidics Device for Cell Capture

A device was produced from a PDMS cast prepared by double casting combined with thermal aging of PDMS. PDMS pre-polymer and curing agent used to make this device are Sylgard® 184 Silicone Elastomer Kit (Ellsworth Adhesives). This process facilitates the appropriate replica of the microcolumns embedded in the capture channel grooves. In this process, an SU-8 master of positive orientation was produced by photolithography first. This SU-8 master then served as mold to cast the first PDMS replica with negative orientation. PDMS casting was achieved by mixing the PDMS pre-polymer with curing agent at a weight ratio of 1:9 and curing the mixture at 70° C. for 3 to 4 hours. The same weight ratio and curing conditions were used during this and the subsequent PDMS castings. The negative PDMS replica resulting from the first casting process was then thermally aged at 80° C. for at least 72 hours. Finally, the thermally aged negative PDMS replica served as a mold to cast a second PDMS replica with positive orientation. Since PDMS pre-polymer is too viscous, volumes are actually measured by weighing the material under the assumption that 1 g=1 ml. Thus, 60 g of Sylgard® 184 Silicone Elastomer pre-polymer and 6.66 g of Sylgard® 184 Silicone Elastomer pre-polymer were measured, mixed, cast and cured. The height of the device once the PDMS slab was bonded to a glass slide was ~4 mm.

The microfluidic units are fabricated by bonding the positive PDMS replica to a glass slide after surface activation of both components by plasma edging. The bonded microfluidic units had width and length dimensions similar to a typical microscope slide, 25 and 75 mm respectively. The glass photomask used to produce the SU-8 master by photolithography during the process described for PDMS double casting prototyping by thermal aging of PDMS contains, printed in chrome, the designed pattern of channels and microstructures with the specified dimensions. That is, each pattern or structure on the design is printed on the surface of the glass photomask with the specified dimensions.

The inlet and outlet reservoirs have a diameter of 2 mm. The inlet reservoir is connected to the capture channels entry side by distribution channels 55 µm in height. Distribution channels were short, vertical channels 1 mm in length and 1.5 mm in width. This channel connects to a long perpendicular channel 8.5 mm in length and 1 mm in width that splits the sample into two sample delivery sections. Each delivery section distributes sample to two of the four capture channels through a vertical channel 4 mm in length and 1.5 mm in width. This vertical channel opens about 45° on each side to gradually increase the cross-sectional flow area and introduce the sample into both capture channels included in the specific delivery section. A similar system of distribution channels facilitates the transport of sample from the exit side of the capture channels to the outlet reservoir for sample removal.

The capture channels are 44 mm in length, 3 mm in width and 55 µm in height. Each capture channel comprises an array of different-shaped microcolumns that include cylindrical, elliptical and a combination of triangular and chevron-like columns arranged in different orientations.

The cylindrical microcolumns included in one of the channels have a diameter of 100 µm, a height of 55 µm and are arranged in hexagonal-shaped units of 370 µm in width and length. Each hexagonal unit is comprised of seven individual cylindrical microcolumns distributed so that six microcolumns sit at each vertex of the hexagon and one microcolumn sits at the center of the hexagon. Individual cylindrical microcolumns are separated 35 µm from neighboring microcolumns within a hexagonal unit. Additionally, individual hexagonal units are separated 50 µm within each row of units and each hexagonal unit is shifted 60 µm horizontally after every row.

Two of the capture channels include capture units that combine triangular and chevron-like microcolumns 55 µm in height. Each of these unique capture units is comprised of two parallel triangular columns with a base and height of 100 µm each and a separation of 50 µm between them. A chevron-like column placed at the base of the parallel triangular microcolumns complements these capture units. These chevron-like columns are 250 µm in length, 50 µm in width and have a 150° aperture angle. In addition, the orientation of the chevron-like columns serves to differentiate the capture units on each of the two channels containing this array. Capture units in which the chevron-like microcolumn points toward the base of the parallel triangular columns, the minimum separation between chevron-like and triangular columns is 35 µm and this type of capture unit is 210 µm in length and 250 µm in width. Differently, combined units where the chevron-like column has the opposite orientation, that is it points away from the base of triangular columns, the minimum separation between the chevron-like and triangular columns is 50 µm and the complete capture unit is 250 µm in length and width. Furthermore, both of these types of capture units are separated 50 µm from neighboring individual units within and between rows, and are shifted 200 µm horizontally every row.

The elliptical microcolumns embedded in the last of the four channels have dimensions of 150 µm, 75 µm and 55 µm for mayor and minor axes and height respectively. Each elliptical microcolumns is separated 50 µm from its neighboring columns within a row and 35 µm from neighboring columns between rows. Elliptical microcolumns shift 100 µm horizontally after every row.

For cell capture, surfaces of the capture channels of the device that come in contact with the flowing sample are coated with capture agent.

EXAMPLE 5

Use of Microfluidics Device for Capturing CTC Using Assay of Method

All surfaces of each capture channel of the device prepared according to Example 4 were coated with capture agent. The capture agent used in this instance consisted of deglycosylated avidin (NeutrAvidin™). Channel surfaces were coated with 10 ng/ml of deglycosylated avidin (NeutrAvidin™) by first injecting 900 µl of a 4% (v/v) (3-mercaptopropyl)trimethoxysilane solution into the device channels and incubating it 45 minutes at room temperature (22° C.). After washing the channels with 2 ml of 100% ethanol, 900 µl of a 0.28% (v/v) GMBS solution was injected into the device and the device was incubated for 35 min at room temperature. The channels were washed again with 2 ml of 100% ethanol followed by 2 ml of ultrapure water and 2 ml of 1× Phosphate Buffered Saline (PBS) solution. Finally, 900 µl of a 10 ng/ml solution of deglycosylated avidin (NeutrAvidin™) were injected into the channels of this device. The device was then stored at 4° C. with its channels filled with the deglycosylated avidin solution until needed. One hour before running a sample through the device, channels were flushed with 2 ml of 1×PBS followed by 1 ml of a 1× Phosphate Buffered Saline (DPBS), 1% (w/v) Bovine Serum Albumin (BSA) and 0.09% (w/v) Sodium Azide. All solutions, including washing solutions, were injected with a continuous flow at a rate of 500 µl/min controlled by a NANOmite syringe pump (Harvard Apparatus).

Figure 9B:
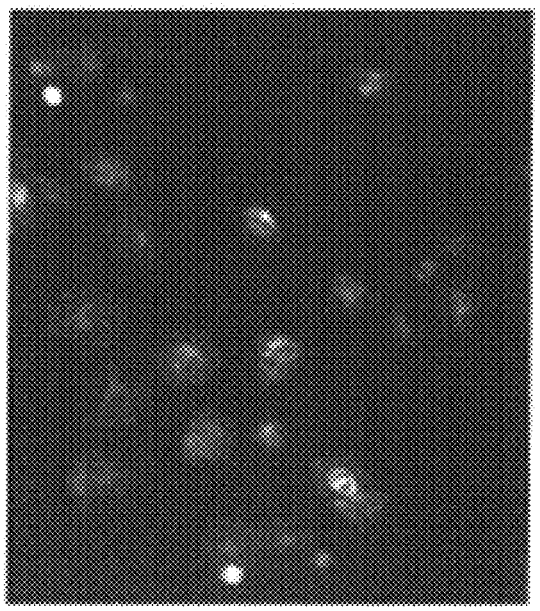
FIGS. 9A-9B are bright field and fluorescence images of U251 cells after 48-hour incubation with $5 \times 10^9$ GC/ml Ad.hTert.pCherry vector and before being run through the microfluidic device. Most of the cells present in the bright field image (FIG. 9A) also appear in the fluorescence image (FIG. 9B) confirming that these cells are expressing the fluorescent fusion protein, pCherry. Fluorescence image was collected at 200 msec of exposure time.
Figure 9A:
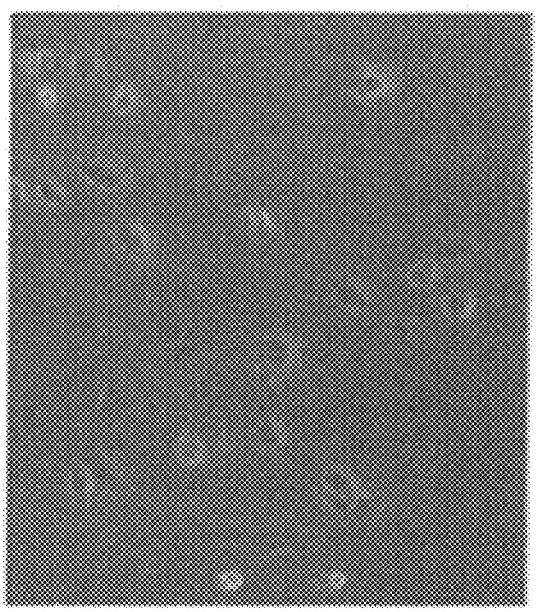
Figure 10C:
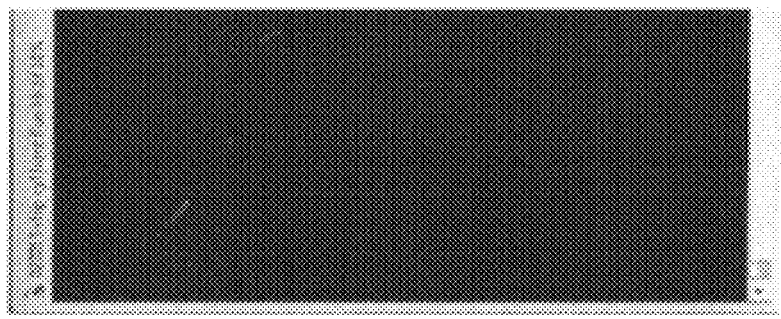
FIGS. 10A-10C illustrates in gray scale sections of tiled images collected for a representative capture channel. Channels are tiled in bright field and fluorescence using the red (FIG. 10B) and blue optic (FIG. 10C) channels, illustrated in gray scale. Bright field images (FIG. 10A) show the capture areas while the images collected with fluorescence channels show either captured cells that selectively express the fluorescent fusion protein, pCherry (infected U251 cells) in the red channel (FIG. 10B) or all captured cells including ones not expressing pCherry (non-infected U251 and Jurkat cells).
Figure 10B:
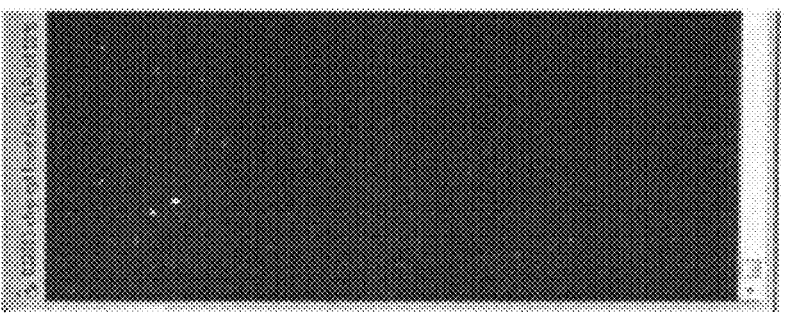
Figure 10A:
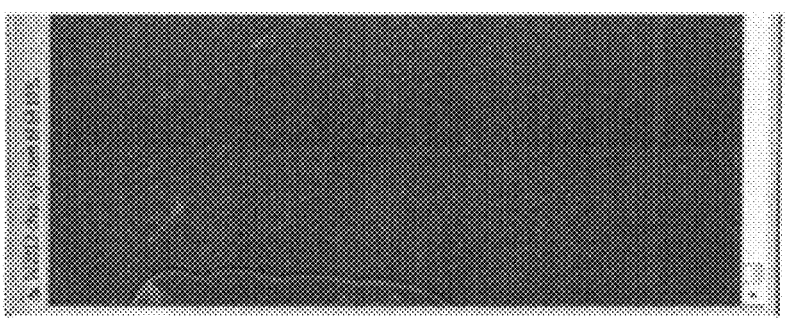

For a proof of principle demonstration of the combined detection process, $5 \times 10^4$ U251 cells were incubated with $5 \times 10^9$ GC/ml of Ad.hTert.pCherry.WPRE.RBG vector for 48 hours at 37° C. with 5% $CO_2$. Most of the cells incubated with the vector were intensively fluorescing after the 2-day incubation period (FIGS. 9A-9B). Cellular fluorescence was an indicator that the infected cells were producing the red fluorescent fusion protein (pCherry) encoded by the vector's genome. To mimic the composition of an enriched sample, the infected U251 cells were mixed with Jurkat cells (not exposed to vector) at a ratio in which infected U251 cells represented 1% of the total cell content of the sample. This cell mixture was then supplemented with biotinylated Anti-pCherry at a final concentration of 10 µg/ml, brought up to a final volume of 500 µl with a 1× Phosphate Buffered Saline (DPBS), 1% (w/v) Bovine Serum Albumin (BSA) and 0.09% (w/v) Sodium Azide solution and incubated on ice for 30 minutes. After the incubation, the volume of the sample was adjusted to 1 ml with plain 1×PBS solution and loaded into a 1 ml syringe. 850 µl of the sample were injected into one of our devices previously functionalized with declycosylated Avidin (NeutrAvidin™) and flushed with 1× Phosphate Buffered Saline (DPBS), 1% (w/v) Bovine Serum Albumin (BSA) and 0.09% (w/v) Sodium Azide solution as described within this document. The sample was injected with a continuous flow at rate of 15 µl/min controlled by a NANOmite syringe pump (Harvard Apparatus). Upon completion of sample injection, device channels were washed twice with 1 ml of 1×PBS to remove cells loosely bound to the channels/microcolumns. To be able to assess purity of the captured sample, the nucleus of trapped cells was stained with the fluorescent dye Hoechst 33342. This was achieved by injecting 400 µl of a 0.5 µM Hoechst 33342 solution immediately after the second 1×PBS wash and incubating the device for 30 minutes at room temperature. After the incubation with Hoechst, the channels of the device were tiled (FIGS. 10A-10C) and captured cells were analyzed using the Eclipse TE2000-U fluorescent microscope (Nikon Corp.) equipped with an automated stage and image analysis programs driven by Image-Pro Plus 7.0 (Media Cybernetics). Representative still pictures of captured cells were also collected under the red (pCherry) and blue (Hoechst) channels as well as under brightfield (FIGS. 11A-11C).

Figure 12:
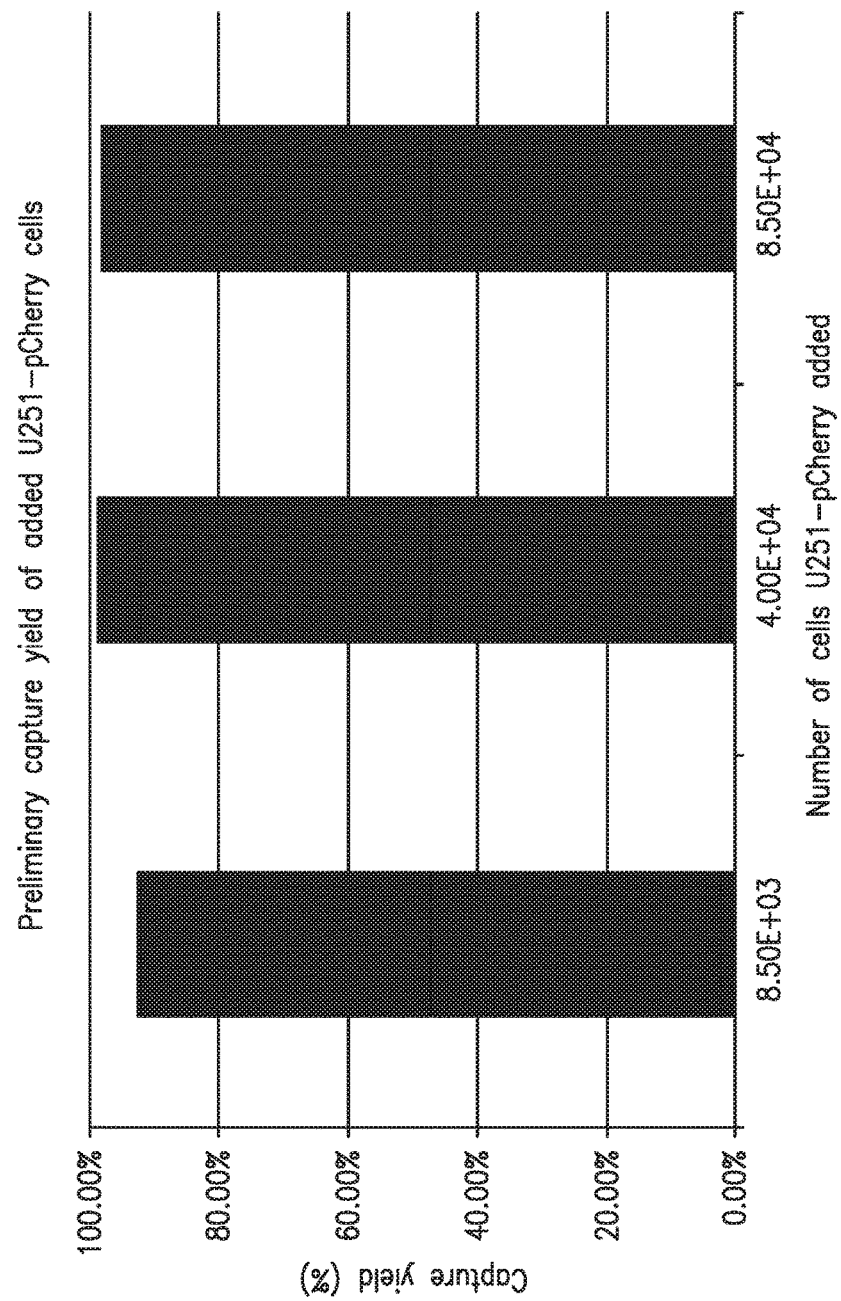
FIG. 12 is a bar chart illustrating preliminary capture yield of the microfluidic device described herein. Capture yield was calculated indirectly by measuring the number of U251 cells positive for pCherry found in the flow-through sample of individual experiments where either $5.5 \times 10^3$, $4 \times 10^4$ or $8.5 \times 10^4$ U251-infected cells (pCherry positive) mixed with $1 \times 10^6$ Jurkat cells were injected into microfluidic devices.

Preliminary data suggests that the rough capture efficiency is about 96% on average. This number is based on the average of three single counts of the flow-through samples collected after the injection of either $5.5 \times 10^3$, $4 \times 10^4$ or $8.5 \times 10^4$ U251-infected cells (pCherry positive) mixed with $1 \times 10^6$ Jurkat cells and 10 µg/ml biotinylated Anti-pCherry into three separate devices at a continuous flowrate of 15 µl/min. The flow-through samples were analyzed and counted using an automated cells counter with fluorescence capabilities (Cellometer Vision, Nexcelom). This instrument counts a 20 µl fraction of the flow-through sample and provides concentrations for the total number of cells found in the sample, by counting under bright field mode and the number of red fluorescent cells by counting cells under a red optic channel. These concentrations were used to indirectly calculate the total number of cells captured based on the number of U251 cells found in the flow-through sample (FIG. 12). Capture efficiency and purity of can be assessed using tiled images collected from the Eclipse TE2000-U fluorescent microscope (Nikon Corp.) and the image analysis programs Image-Pro Plus 7.0 (Media Cybernetics).

All publications cited in this specification are incorporated herein by reference, as is priority application U.S. Ser. No. 14/438,321, filed Apr. 24, 2015, PCT/US2013/031698, filed Mar. 14, 2013, U.S. 61/718,993, filed Oct. 26, 2012. While the invention has been described with reference to particular embodiments, it will be appreciated that modifications can be made without departing from the spirit of the invention. Such modifications are intended to fall within the scope of the appended claims.

The invention claimed is:

1. A method for detecting circulating tumor cells in vitro, said method comprising
    (a) combining a test sample from a patient suspected of having circulating tumor cells, and a non-lytic adenoviral system, and culture media for the cells, said adenoviral system comprising:
        (i) a first replication-defective adenoviral particle having an adenoviral capsid in which an expression cassette is packaged, said expression cassette comprising an adenoviral 5' ITR, a tumor-specific promoter which is specifically activated in circulating tumor cells, and an adenoviral 3' ITR, wherein said adenoviral particle is rendered replication defective and non-lytic by a deletion in one or more adenoviral early genes; and
        (ii) a coding sequence for a reporter protein which is expressed in circulating tumor cells, and an adenoviral 3' ITR;
    (b) incubating the test sample and the non-lytic adenoviral system for a sufficient time to permit expression of the reporter protein,
    optionally replenishing the media; and
    (c) measuring reporter protein expression in the test samples and optionally repeating (c), whereby presence of reporter expression indicates the presence of circulating tumor cells in the sample,
    wherein (a) to (c) are performed a second time using a non-lytic adenoviral system having a different reporter protein.

2. The method according to claim 1, wherein the promoter is selected from a human telomerase reverse transcriptase (hTERT), a human telomerase RNA (hTR), a hTERC promoter, or a progression elevated gene promoter (PEG-Prom).

3. The method according to claim 1 wherein the measuring (c) is performed eighteen to ninety-six hours after first combining the adenoviral system and the test sample.

4. The method according to claim 3, wherein the measuring (c) is performed twenty-four to thirty-six hours after first combining the adenoviral system and the test sample.

5. The method according to claim 1, wherein the different reporter protein is under the control of a different tumor specific promoter.

6. The method according to claim 1, wherein the first replication-defective adenoviral particle comprises a deletion in E1a and/or E1b genes and further comprises an E3 gene deletion.

7. The method according to claim 1, wherein the expression cassette of the first replication-defective adenoviral particle further comprises (ii) the coding sequence for the reporter protein.

8. The method according to claim 1, wherein the first replication-defective adenoviral particle (i) further comprises a coding sequence for an endonuclease, and wherein the coding sequence for the reporter protein (ii) is under the control of a reporter expression cassette which comprises expression control sequences upstream of the coding sequence for the reporter protein and endonuclease recognition sites located both 5' and 3' to the coding sequence for the reporter protein and the upstream expression control sequences.

9. The method according to claim 8, wherein the reporter expression cassette (ii) is on a second replication-defective adenoviral particle.

10. The method according to claim 9, wherein the expression cassette of (i) is in the site of a deletion in the E1a and/or E1b coding sequence.

11. The method according to claim 9, wherein the reporter expression cassette (ii) is carried by the first replication-defective adenoviral particle.

12. The method according to claim 11, wherein the reporter expression cassette is in the site of a deletion in the E3.

13. The method according to claim 8, wherein the endonuclease is a selected from a recombinase, an integrase, an invertase, and a resolvase.

14. The method according to claim 13, wherein the endonuclease is a Cre recombinase and the recognition sites are loxP sites.

15. The method according to claim 9, wherein the reporter protein is selected from the group consisting of a green fluorescent protein, enhanced green fluorescent protein, mCherry, red fluorescent protein, red fluorescent protein-turbo.

16. The method according to claims 9, further comprising enriching a blood sample from the patient prior to combining it with the non-lytic adenoviral system.

17. The method according to claim 9, wherein the blood sample is enriched by:
  obtaining a whole blood sample from a patient;
  combining the whole blood sample with neutral buffered saline in a tube containing a separation system comprising a density gradient separation fluid and a rigid but porous disk, the tube having a conical bottom;
  centrifuging the tube for about 10 minutes to about 60 minutes at about 500 relative centrifugal force (RCF) units to about 3000 RCF units to separate a CTC-enriched layer from the whole blood sample;
  harvesting the CTC-enriched layer to obtain a CTC-enriched pellet suspension;
  incubating the pellet suspension in a water bath;
  introducing cell culture media to allow pellet suspension in preparation for the adenoviral system.

18. The method according to claim 17, wherein the whole blood sample is about 1 mL to about 15 mL.

19. The method according to claim 18, wherein the whole blood sample is 10 mL.

20. The method according to claim 18, wherein the buffered saline is phosphate buffered saline.

21. The method according to claim 18, wherein the whole blood sample is combined with an equal volume of the buffered saline.

22. The method according to claim 18, wherein the whole blood and buffered saline are chilled to about 0° C. to about 4° C. prior to centrifuging.

23. The method according to claim 18, wherein centrifuging is performed at about 20 minutes at about 1500 RCF units.

24. The method according to claim 18, wherein following collection of the CTC-enriched pellet suspension, the remaining solution is extracted and placed in a separate conical tube and the first conical is washed to collect any residual CTCs.

25. A method for detecting circulating tumor cells in vitro, said method comprising
  (a) combining a test sample from a patient suspected of having circulating tumor cells, and a non-lytic adenoviral system, and culture media for the cells, said adenoviral system comprising:
    (i) a first replication-defective adenoviral particle having an adenoviral capsid in which an expression cassette is packaged, said expression cassette comprising an adenoviral 5' ITR, a tumor-specific promoter which is specifically activated in circulating tumor cells, and an adenoviral 3' ITR, wherein said adenoviral particle is rendered replication defective and non-lytic by a deletion in one or more adenoviral early genes; and
    (ii) a coding sequence for a reporter protein which is expressed in circulating tumor cells, and an adenoviral 3' ITR;
  (b) incubating the test sample and the non-lytic adenoviral system for a sufficient time to permit expression of the reporter protein,
    optionally replenishing the media; and
  (c) measuring reporter protein expression in the test samples and optionally repeating (c), whereby presence of reporter expression indicates the presence of circulating tumor cells in the sample,
    wherein the first replication-defective adenoviral particle comprises a deletion in E1a and/or E1b genes and further comprises an E3 gene deletion.

26. A method for detecting circulating tumor cells in vitro, said method comprising
  (a) combining a test sample from a patient suspected of having circulating tumor cells, and a non-lytic adenoviral system, and culture media for the cells, said adenoviral system comprising:
    (i) a first replication-defective adenoviral particle having an adenoviral capsid in which an expression cassette is packaged, said expression cassette comprising an adenoviral 5' ITR, a tumor-specific promoter which is specifically activated in circulating tumor cells, and an adenoviral 3' ITR, wherein said adenoviral particle is rendered replication defective and non-lytic by a deletion in one or more adenoviral early genes; and
    (ii) a coding sequence for a reporter protein which is expressed in circulating tumor cells, and an adenoviral 3' ITR;
  (b) incubating the test sample and the non-lytic adenoviral system for a sufficient time to permit expression of the reporter protein,
    optionally replenishing the media; and (c) measuring reporter protein expression in the test samples and optionally repeating (c), whereby presence of reporter expression indicates the presence of circulating tumor cells in the sample,
wherein the expression cassette of the first replication-defective adenoviral particle further comprises (ii) the coding sequence for the reporter protein.

27. A method for detecting circulating tumor cells in vitro, said method comprising
(a) combining a test sample from a patient suspected of having circulating tumor cells, and a non-lytic adenoviral system, and culture media for the cells, said adenoviral system comprising:
    (i) a first replication-defective adenoviral particle having an adenoviral capsid in which an expression cassette is packaged, said expression cassette comprising an adenoviral 5' ITR, a tumor-specific promoter which is specifically activated in circulating tumor cells, and an adenoviral 3' ITR, wherein said adenoviral particle is rendered replication defective and non-lytic by a deletion in one or more adenoviral early genes; and
    (ii) a coding sequence for a reporter protein which is expressed in circulating tumor cells, and an adenoviral 3' ITR;
(b) incubating the test sample and the non-lytic adenoviral system for a sufficient time to permit expression of the reporter protein,
optionally replenishing the media; and
(c) measuring reporter protein expression in the test samples and optionally repeating (c), whereby presence of reporter expression indicates the presence of circulating tumor cells in the sample,
wherein the first replication-defective adenoviral particle (i) further comprises a coding sequence for an endonuclease, and wherein the coding sequence for the reporter protein (ii) is under the control of a reporter expression cassette which comprises expression control sequences upstream of the coding sequence for the reporter protein and endonuclease recognition sites located both 5' and 3' to the coding sequence for the reporter protein and the upstream expression control sequences.

28. The method according to claim 27, wherein the reporter expression cassette (ii) is on a second replication-defective adenoviral particle.

29. The method according to claim 28, wherein the expression cassette of (i) is in the site of a deletion in the E1a and/or E1b coding sequence.

30. The method according to claim 28, wherein the reporter expression cassette (ii) is carried by the first replication-defective adenoviral particle.

31. The method according to claim 30, wherein the reporter expression cassette is in the site of a deletion in the E3.

32. The method according to claim 27, wherein the endonuclease is a selected from a recombinase, an integrase, an invertase, and a resolvase.

33. The method according to claim 32, wherein the endonuclease is a Cre recombinase and the recognition sites are loxP sites.

34. The method according to claim 28, wherein the reporter protein is selected from a green fluorescent protein, enhanced green fluorescent protein, mCherry, red fluorescent protein, or a red fluorescent protein-turbo.

35. The method according to claims 28, further comprising enriching a blood sample from the patient prior to combining it with the non-lytic adenoviral system.

36. The method according to claim 28, wherein the blood sample is enriched by:
    obtaining a whole blood sample from a patient;
    combining the whole blood sample with neutral buffered saline in a tube containing a separation system comprising a density gradient separation fluid and a rigid but porous disk, the tube having a conical bottom;
    centrifuging the tube for about 10 minutes to about 60 minutes at about 500 relative centrifugal force (RCF) units to about 3000 RCF units to separate a CTC-enriched layer from the whole blood sample;
    harvesting the CTC-enriched layer to obtain a CTC-enriched pellet suspension;
    incubating the pellet suspension in a water bath;
    introducing cell culture media to allow pellet suspension in preparation for the adenoviral system.

37. The method according to claim 36, wherein the whole blood sample is about 1 mL to about 15 mL.

38. The method according to claim 37, wherein the whole blood sample is 10 mL.

39. The method according to claim 37, wherein the buffered saline is phosphate buffered saline.

40. The method according to claim 37, wherein the whole blood sample is combined with an equal volume of the buffered saline.

41. The method according to claim 37, wherein the whole blood and buffered saline are chilled to about 0° C. to about 4° C. prior to centrifuging.

42. The method according to claim 37, wherein centrifuging is performed at about 20 minutes at about 1500 RCF units.

43. The method according to claim 37, wherein following collection of the CTC-enriched pellet suspension, the remaining solution is extracted and placed in a separate conical tube and the first conical is washed to collect any residual CTCs.

* * * * *